United States Patent
Kassab

(10) Patent No.: US 9,351,661 B2
(45) Date of Patent: *May 31, 2016

(54) DEVICES, SYSTEMS, AND METHODS TO MEASURE PARALLEL TISSUE CONDUCTANCE, LUMINAL CROSS-SECTIONAL AREAS, FLUID VELOCITY, AND/OR DETERMINE PLAQUE VULNERABILITY USING TEMPERATURE

(71) Applicant: 3DT Holdings, LLC, Zionsville, IN (US)

(72) Inventor: Ghassan S. Kassab, Zionsville, IN (US)

(73) Assignee: 3DT Holdings, LLC, San Diego, CA (US)

( * ) Notice: Subject to any disclaimer, the term of this patent is extended or adjusted under 35 U.S.C. 154(b) by 36 days.

This patent is subject to a terminal disclaimer.

(21) Appl. No.: 14/258,920

(22) Filed: Apr. 22, 2014

(65) Prior Publication Data

US 2014/0222129 A1    Aug. 7, 2014

Related U.S. Application Data

(63) Continuation of application No. 12/701,368, filed on Feb. 5, 2010, now Pat. No. 8,706,209.

(51) Int. Cl.
*A61B 5/05* (2006.01)
*A61B 5/053* (2006.01)
(Continued)

(52) U.S. Cl.
CPC ............... *A61B 5/0538* (2013.01); *A61B 5/01* (2013.01); *A61B 5/02007* (2013.01);
(Continued)

(58) Field of Classification Search
CPC .................................................... A61B 5/0538

USPC ......... 600/547, 549, 505, 526, 587, 481, 486, 600/454, 561, 485, 490, 506, 593; 606/192, 606/194, 198; 128/898; 424/439; 607/72; 623/1.11

See application file for complete search history.

(56) References Cited

U.S. PATENT DOCUMENTS 3,896,373 A    7/1975  Zelby
4,587,974 A    5/1986  Link
(Continued)

FOREIGN PATENT DOCUMENTS

EP    1 025 805 A1    8/2000
WO    WO 98/35611 A1    8/1998
(Continued)

OTHER PUBLICATIONS

PCT/US04/04828, PCT Search Report and Written Opinion dated Jul. 6, 2005.

(Continued)

*Primary Examiner* — Brian Szmal
(74) *Attorney, Agent, or Firm* — Reichel Stohry LLP; Mark C. Reichel; Natalie J. Dean

(57) ABSTRACT

Devices, systems, and methods to measure parallel tissue conductance, luminal cross-sectional areas, fluid velocity, and/or determine plaque vulnerability using temperature. In at least one embodiment of a method to obtain parallel tissue conductance, the method comprises the steps of inserting at least part of a detection device into a luminal organ, applying current thereto, obtaining a native temperature measurement, injecting a solution of a known conductivity into the luminal organ, detecting a temperature change indicative of the fluid within the luminal organ, measuring an output conductance, and calculating a parallel tissue conductance based upon the output conductance and the conductivity of the injected solution.

20 Claims, 17 Drawing Sheets

(51) Int. Cl.
  *A61B 5/02*    (2006.01)
  *A61B 5/028*   (2006.01)
  *A61B 5/00*    (2006.01)
  *G01K 13/00*   (2006.01)
  *A61B 5/01*    (2006.01)
  *A61B 5/107*   (2006.01)
  *A61F 2/958*   (2013.01)

(52) U.S. Cl.
  CPC .............. *A61B 5/028* (2013.01); *A61B 5/1076* (2013.01); *A61B 5/6851* (2013.01); *A61B 5/6853* (2013.01); *A61F 2/958* (2013.01); *G01K 13/002* (2013.01)

(56) References Cited

U.S. PATENT DOCUMENTS

| | | |
|---|---|---|
| 4,840,182 A | 6/1989 | Carlson |
| 4,947,110 A | 8/1990 | Laass |
| 5,058,583 A | 10/1991 | Geddes et al. |
| 5,125,410 A | 6/1992 | Misono et al. |
| 5,233,994 A | 8/1993 | Shmulewitz |
| 5,366,443 A | 11/1994 | Eggers et al. |
| 5,453,576 A | 9/1995 | Krivitski |
| 5,665,103 A | 9/1997 | Lafontaine et al. |
| 5,971,933 A | 10/1999 | Schlueter et al. |
| 6,112,115 A | 8/2000 | Feldman et al. |
| 6,165,977 A | 12/2000 | Mochly-Rosen |
| 6,187,744 B1 | 2/2001 | Rooney |
| 6,191,136 B1 | 2/2001 | Marban |
| 6,270,493 B1 | 8/2001 | Lalonde et al. |
| 6,296,615 B1 | 10/2001 | Brockway et al. |
| 6,325,762 B1 | 12/2001 | Tjin |
| 6,354,999 B1 | 3/2002 | Dgany et al. |
| 6,360,123 B1 | 3/2002 | Kimchi et al. |
| 6,471,656 B1 | 10/2002 | Shalman et al. |
| 6,494,832 B1 | 12/2002 | Feldman et al. |
| 6,511,413 B2 | 1/2003 | Landesberg |
| 6,545,678 B1 | 4/2003 | Ohazama |
| 6,569,862 B1 | 5/2003 | Marban |
| 6,663,661 B2 | 12/2003 | Boneau |
| 6,666,828 B2 | 12/2003 | Greco et al. |
| 6,926,674 B2 | 8/2005 | Tenerz et al. |
| 7,069,072 B2 | 6/2006 | Jensen et al. |
| 7,141,019 B2 | 11/2006 | Pearlman |
| 7,169,107 B2 | 1/2007 | Jersey-Willuhn et al. |
| 7,189,208 B1 | 3/2007 | Beatty et al. |
| 7,236,820 B2 | 6/2007 | Mabary et al. |
| 7,311,702 B2 | 12/2007 | Tallarida et al. |
| 7,326,241 B2 | 2/2008 | Jang |
| 8,706,209 B2 * | 4/2014 | Kassab ..................... 600/547 |
| 2002/0049488 A1 | 4/2002 | Boneau |
| 2003/0013986 A1 | 1/2003 | Saadat |
| 2004/0024329 A1 | 2/2004 | Jansen et al. |
| 2004/0044286 A1 | 3/2004 | Hossack et al. |
| 2004/0116816 A1 | 6/2004 | Tenerz et al. |
| 2007/0161914 A1 | 7/2007 | Zdeblick et al. |
| 2008/0176271 A1 | 7/2008 | Silver et al. |
| 2008/0194996 A1 | 8/2008 | Kassab |
| 2008/0269581 A1 | 10/2008 | Wood et al. |
| 2009/0105799 A1 | 4/2009 | Hekmat et al. |

FOREIGN PATENT DOCUMENTS

| | | |
|---|---|---|
| WO | WO 02/19905 | 3/2002 |
| WO | WO 02/085442 A1 | 10/2002 |
| WO | WO 03/092495 A1 | 11/2003 |

OTHER PUBLICATIONS

Hoekstein and Inbar, "Cardiac Stroke Volume Estimation from Two Electrodes Electrical Impedance Measurements." Technion Department of Electrical Engineering Publication EE PUB No. 911, Feb. 1994.

L. Kornet, J.R.C. Jansen, E.J. Gussenhoven, M.R. Hardeman A.P.G. Hoeks and A. Versprille, "Conductance Method for the Measurement of Cross-Sectional Areas of the Aorta," Annals of Biomedical Engineering, vol. 27, pp. 141-150, 1999.

Douglas A. Hettrick, Joseph Battocietti, James Ackmann, and David C. Warltier, "Finite Element Model Determination of Correction Factors Used for Measurement of Aorta Diameter via Conductance," Annals of Biomedical Engineering, vol. 27, pp. 151-159, 1999.

Douglas A. Hettrick, Joseph Battocletti, James Ackmann, John Linehan, and David C. Warltier, "In Vivo Measurement of Real-Time Aortic Segmental Volume Using the Conductance Catheter," Annals of Biomedical Engineering, vol. 26, pp. 431-440, 1998.

PCT/US06/05985, PCT Search Report and Written Opinion dated Aug. 8, 2007.

Supplementary European Search Report for EP Application Serial No. EP 04 71 2383 to Electro-Cat, LLC, dated Aug. 6, 2007.

PCT/US11/23911, PCT Search Report and Written Opinion dated Apr. 4, 2011.

* cited by examiner

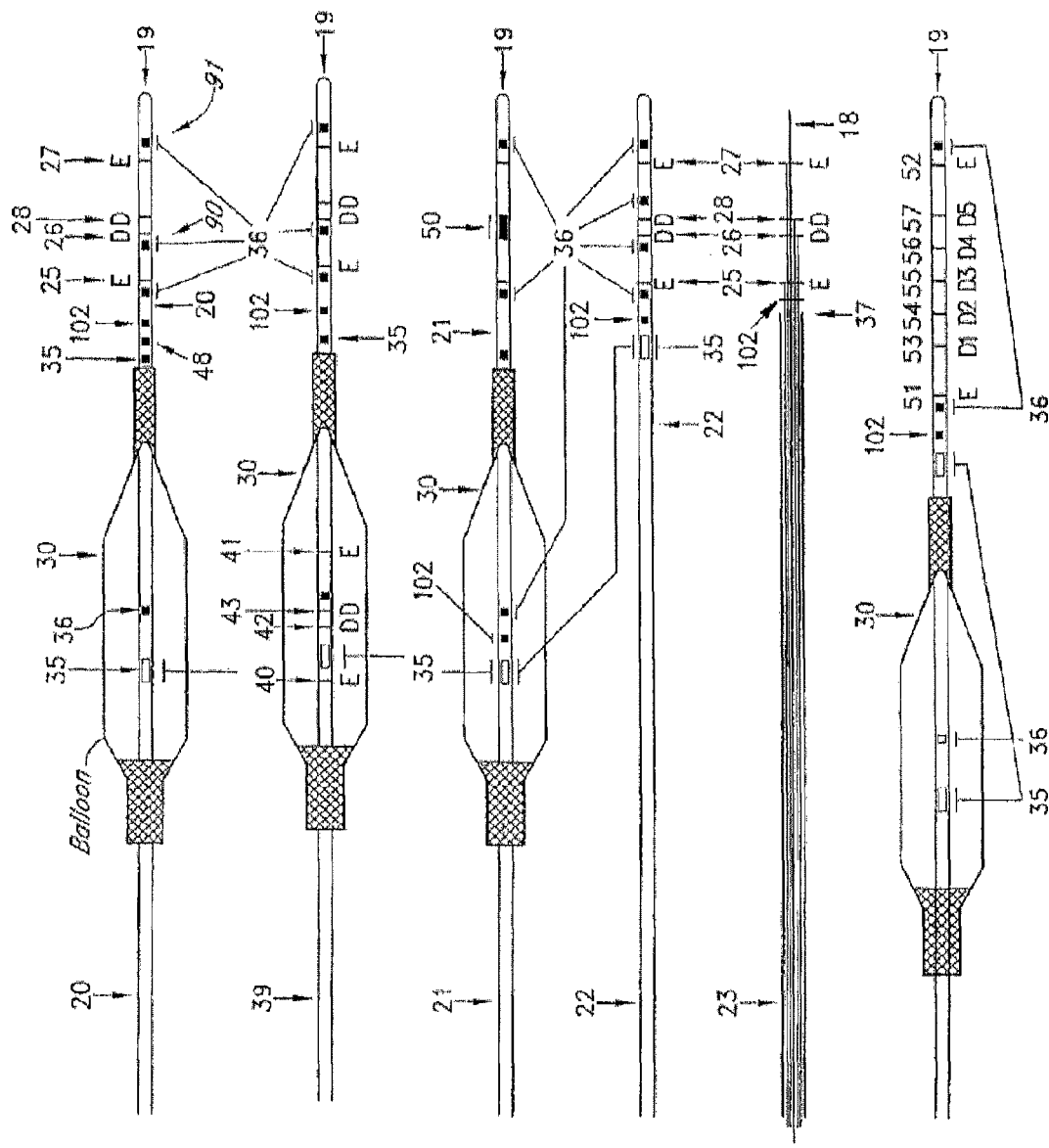

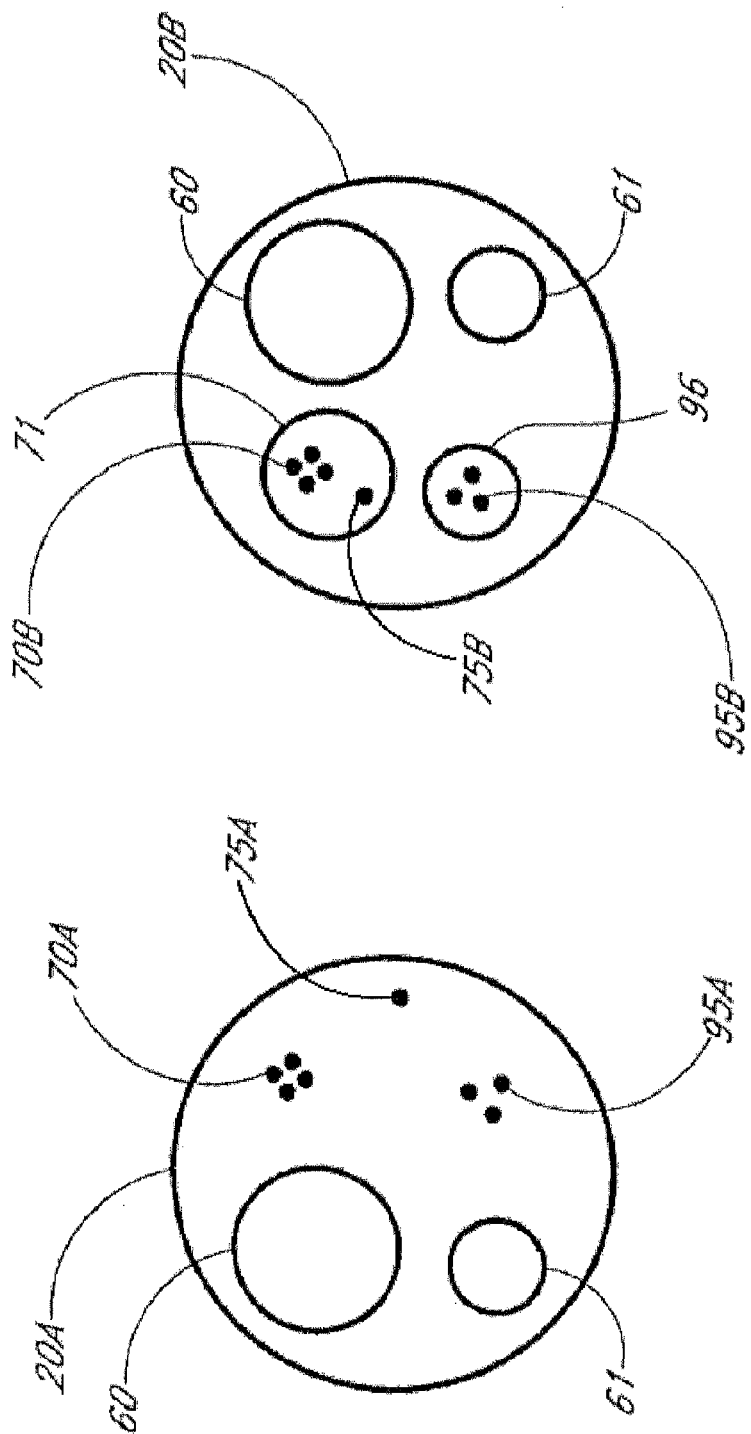

DEVICES, SYSTEMS, AND METHODS TO MEASURE PARALLEL TISSUE CONDUCTANCE, LUMINAL CROSS-SECTIONAL AREAS, FLUID VELOCITY, AND/OR DETERMINE PLAQUE VULNERABILITY USING TEMPERATURE

PRIORITY

The present application is related to, claims the priority benefit of, and is a U.S. continuation patent application of, U.S. patent application Ser. No. 12/701,368, filed Feb. 5, 2010 and issued as U.S. Pat. No. 8,706,209 on Apr. 22, 2014, the contents of which are hereby incorporated by reference in their entirety into this disclosure.

BACKGROUND

Coronary heart disease (CHD) is commonly caused by atherosclerotic narrowing of the coronary arteries and is likely to produce angina pectoris, heart attacks or a combination. CHD caused 466,101 deaths in the USA in 1997 and is one of the leading causes of death in America today. To address CHD, intra-coronary stents have been used in large percentages of CHD patients. Stents increase the minimal coronary lumen diameter to a greater degree than percutaneous transluminal coronary angioplasty (PTCA) alone.

Intravascular ultrasound is a method of choice to determine the true diameter of a diseased vessel in order to size the stent correctly. The tomographic orientation of ultrasound enables visualization of the full 360° circumference of the vessel wall and permits direct measurements of lumen dimensions, including minimal and maximal diameter and cross-sectional area. Information from ultrasound is combined with that obtained by angiography. Because of the latticed characteristics of stents, radiographic contrast material can surround the stent, producing an angiographic appearance of a large lumen, even when the stent struts are not in full contact with the vessel wall. A large observational ultrasound study after angiographically guided stent deployment revealed an average residual plaque area of 51% in a comparison of minimal stent diameter with reference segment diameter, and incomplete wall apposition was frequently observed. In this cohort, additional balloon inflations resulted in a final average residual plaque area of 34%, even though the final angiographic percent stenosis was negative (20.7%). Those investigators used ultrasound to guide deployment.

However, using intravascular ultrasound as mentioned above requires a first step of advancement of an ultrasound catheter and then withdrawal of the ultrasound catheter before coronary angioplasty thereby adding additional time to the stent procedure. Furthermore, it requires an ultrasound machine. This adds significant cost and time and more risk to the procedure.

One common type of coronary artery disease is atherosclerosis, which is a systemic inflammatory disease of the vessel wall that affects multiple arterial beds, such as aorta, carotid and peripheral arteries, and causes multiple coronary artery lesions and plaques. Atherosclerotic plaques typically include connective tissue, extracellular matrix (including collagen, proteoglycans, and fibronectin elastic fibers), lipid (crystalline cholesterol, cholesterol esters and phospholipids), and cells such as monocyte-derived macrophages, T lymphocytes, and smooth muscles cells. A wide range of plaques occurs pathologically with varying composition of these components.

A process called "positive remodeling" occurs early on during the development of atherosclerosis in coronary artery disease (CAD) where the lumen cross-sectional area (CSA) stays relatively normal because of the expansion of external elastic membrane and the enlargement of the outer CSA. However, as CAD progresses, there is no further increase in the external diameter of the external elastic membrane. Instead, the plaque begins to impinge into the lumen and decreases the lumen CSA in a process called "negative remodeling".

Evidence shows that that a non-significant coronary atherosclerotic plaque (typically <50% stenosis) can rupture and produce myocardial infarct even before it produces significant lumen narrowing if the plaque has a particular composition. For example, a plaque with a high concentration of lipid and a thin fibrous cap may be easily sheared or ruptured and is referred to as a "vulnerable" plaque. In contrast, "white" plaques are less likely to rupture because the increased fibrous content over the lipid core provides stability ("stable" plaque). A large lipid core (typically >40%) rich in cholesterol is at a high risk for rupture and is considered a "vulnerable" plaque. In summary, plaque composition appears to determine the risk of acute coronary syndrome more so than the standard degree of stenosis because a higher lipid core is a basic characteristic of a higher risk plaque.

Conventionally, angiography has been used to visualize and characterize atherosclerotic plaque in coronary arteries. Because of the recent finding that plaque composition, rather than severity of stenosis, determines the risk for acute coronary syndromes, newer imaging modalities are required to distinguish between and determine the composition of "stable" and "vulnerable" plaques. Although a number of invasive and noninvasive imaging techniques are available to assess atherosclerotic vessels, most of the standard techniques identify luminal diameter, stenosis, wall thickness and plaque volume. To date, there is no standard method that can characterize plaque composition (e.g., lipid, fibrous, calcium, or thrombus) and therefore there is no routine and reliable method to identify the higher risk plaques.

Noninvasive techniques for evaluation of plaque composition include magnetic resonance imaging (MRI). However, MRI lacks the sufficient spatial resolution for characterization of the atherosclerotic lesion in the coronary vessel. Minimally invasive techniques for evaluation of plaque composition include intravascular ultrasound (IVUS), optical coherence tomography (OCT), raman and infrared spectroscopy. Thermography is also a catheter-based technique used to detect the vulnerable plaques on the basis of temperature difference caused by the inflammation in the plaque. Using the various catheter-based techniques requires a first step of advancement of an IVUS, OCT, or thermography catheter and then withdrawal of the catheter before coronary angioplasty thereby adding additional time and steps to the stent procedure. Furthermore, these devices require expensive machinery and parts to operate. This adds significant cost and time and more risk to the procedure.

Thus, a need exists in the art for an alternative to the conventional methods of determining cross-sectional area of a luminal organ and determining the vulnerability of a plaque present within a luminal organ. A further need exist for a reliable, accurate and minimally invasive system or technique of determining the same.

BRIEF SUMMARY

In at least one embodiment of a method to obtain a parallel tissue conductance within a luminal organ of the present disclosure, the method comprises the steps of introducing at least part of a detection device into a luminal organ at a first location, the detection device having a detector and a thermistor positioned relative to the detector, applying current to the detection device using a stimulator, obtaining a first temperature measurement of a fluid native to the first location, injecting a solution having a known conductivity into the luminal organ at or near the detector of the detection device, detecting a temperature change at the first location indicative of the injected solution, measuring an output conductance in connection with the injected solution based upon the detected temperature change, and calculating a parallel tissue conductance at the first location based in part upon the output conductance and the conductivity of the injected solution. In at least another method, the step of calculating a parallel tissue conductance comprises the step of calculating a cross-sectional area of the luminal organ at the first location.

In at least one embodiment of a method to assess the vulnerability of a plaque within a luminal organ of the present disclosure, the method comprises the steps of introducing at least part of a detection device into a luminal organ at a plaque site, the detection device having a thermistor, injecting a solution into the luminal organ at or near the thermistor of the detection device, detecting a first temperature measurement at the plaque site indicative of a plaque and the injected solution, and determining vulnerability of the plaque at the plaque site based in part upon the first temperature at the plaque site. In at least one embodiment, the step of detecting a first temperature measurement is performed using the thermistor.

In at least one embodiment of a device to obtain a parallel tissue conductance within a luminal organ of the present disclosure, the device comprises an elongated body having a longitudinal axis extending from a proximal end to a distal end, a pair of excitation electrodes located on the elongated body, a pair of detection electrodes located on the elongated body in between the pair of excitation electrodes, and a thermistor positioned along the longitudinal axis, located near the distal end and positioned proximal to the first excitation electrode and the second excitation electrode. In at least another embodiment, at least one excitation electrode of the pair of excitation electrodes is/are in communication with a current source operable to supply electrical current to the at least one excitation electrode. In another embodiment, the device further comprises a data acquisition and processing system capable of receiving conductance data from the pair of detection electrodes, wherein, in at least one embodiment, the data acquisition and processing system is further capable of calculating a parallel tissue conductance based in part upon the conductance data and a known conductivity of a solution injected into a luminal organ at or near the pair of detection electrodes.

In at least one embodiment of a device to assess the vulnerability of a plaque within a luminal organ of the present disclosure, the device comprise an elongated body having a longitudinal axis extending from a proximal end to a distal end, and a thermistor positioned along the longitudinal axis located near the distal end of the elongated body. In at least another embodiment, the device further comprises a data acquisition and processing system capable of receiving temperature data from the thermistor.

In at least one embodiment of a system to obtain a parallel tissue conductance within a luminal organ of the present disclosure, the system comprises a detection device having a detector and a thermistor positioned relative to the detector, and a current source coupled to the detector and the thermistor.

In at least one embodiment of a system to assess the vulnerability of a plaque within a luminal organ of the present disclosure, the system comprises an elongated body having a longitudinal axis extending from a proximal end to a distal end, a thermistor positioned along the longitudinal axis located near the distal end of the elongated body, and a thermistor excitation device coupled to the thermistor.

BRIEF DESCRIPTION OF THE DRAWINGS

FIG. 2B shows an exemplary detection device of an exemplary system having impedance measuring electrodes supported in front of a stenting balloon thereon, according to an embodiment of the present disclosure;

FIG. 2C shows an exemplary detection device of an exemplary system having impedance measuring electrodes within and in front of a balloon thereon, according to an embodiment of the present disclosure;

FIG. 2D shows an exemplary detection device of an exemplary having an ultrasound transducer within and in front of a balloon thereon, according to an embodiment of the present disclosure;

FIG. 2E shows an exemplary detection device of an exemplary system without a stenting balloon, according to an embodiment of the present disclosure;

FIG. 2F shows an exemplary detection device of an exemplary system having wire and impedance electrodes, according to an embodiment of the present disclosure;

FIG. 2G shows an exemplary detection device of an exemplary system having multiple detection electrodes, according to an embodiment of the present disclosure;

FIGS. 2H and 2I show at least a portion of exemplary systems according to embodiments of the present disclosure;

DETAILED DESCRIPTION

Figure 1A:
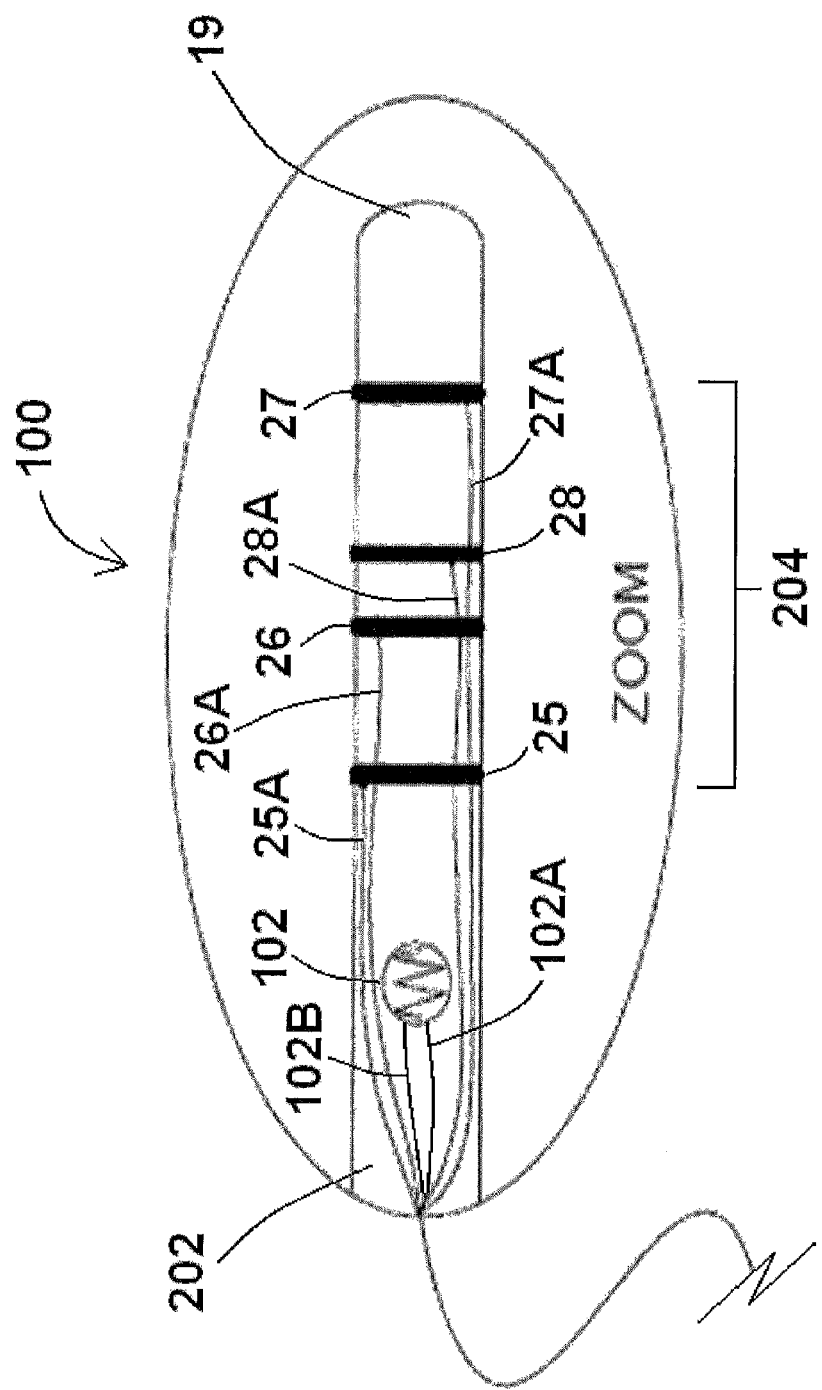
FIGS. 1A and 1B show at least a portion of an exemplary detection devices for obtaining parallel tissue conductance, measuring luminal cross-sectional areas, measuring fluid velocity, and/or determining plaque vulnerability using temperature within a luminal organ, said device having a thermistor, according to an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

At least a portion of an exemplary embodiment of a device for obtaining parallel tissue conductance, measuring luminal cross-sectional areas, measuring fluid velocity, and/or determining plaque vulnerability using temperature of the present disclosure is shown in FIG. 1A. As shown in FIG. 1A, an exemplary device 100 comprises a detector 204 for detecting conductance within a luminal organ. Detector 204, along with other components of device 100, are shown in an enlarged view in FIG. 1A noting that, for example, device 100 may comprise any number of catheters or wires with the components referenced herein, including, but not limited to, pressure wires, guide wires, or guide catheters. Detector 204, in at least one embodiment, is positioned along an elongated body 202 of device 100, wherein elongated body 202 has a longitudinal axis, a proximal end (further from detector 204), and a distal end (closer to detector 204).

In at least one embodiment of a device 100 of the present application, detector 204 is positioned along elongated body 202 of device 100 at or near the distal end ("tip") 19 of device 100. In an exemplary embodiment, and as shown in FIG. 1A, detector 204 of device 100 comprises detection electrodes 26, 28 positioned in between excitation electrodes 25, 27, wherein excitation electrodes 25, 27 are capable of producing an electrical field. As shown in FIG. 1A, excitation electrodes 25, 27 may comprise wires 25A and 27A, respectively, coupled thereto to facilitate the operation of excitation electrodes 25, 27 by a user. Similarly, detection electrodes 26, 28 may comprise wires 26A and 28A, respectively, coupled thereto to facilitate the operation of detection electrodes 26, 28 by a user. Wires 25A, 26A, 27A, and 28A may further couple to system console 250 (as shown in FIG. 2) so that, for example, activation of excitation electrodes 25, 27 and the acquisition of conductance information from detection electrodes 26, 28 may be controlled.

As shown in FIG. 1A, an exemplary device 100 of the present disclosure comprises a thermistor (temperature sensor) 102 coupled thereto, whereby thermistor 102 is connected to, for example, console 250 (as shown in FIG. 2) by way of thermistor wires 102A and 102B. Thermistor wires 102A and 102B, as well as wires 25A, 26A, 27A, and 28A, may be coupled to console 250, as referenced above, or to any number of other components of an exemplary system 200 of the present disclosure so that thermistor 102, excitation electrodes 25, 27, and detection electrodes 26, 28 may operate and/or provide data to user in accordance with the present disclosure. In an exemplary embodiment, thermistor wire 102A provides current to thermistor 102 to allow thermistor 102 to operate and detect temperature, while thermistor wire 102B provides temperature data to console 250, or vice versa. In at least one embodiment of a device 100, wires 25A, 26A, 27A, 28A, 102A and/or 102B may have insulated electrical wire connections that run through, for example, a lumen of device 100 and the proximal end of elongated body 102. In at least another embodiment, wires 25A, 26A, 27A, 28A, 102A and/or 102B may be embedded within elongated body 102 so that each wire is insulated from the other wires.

Figure 1B:
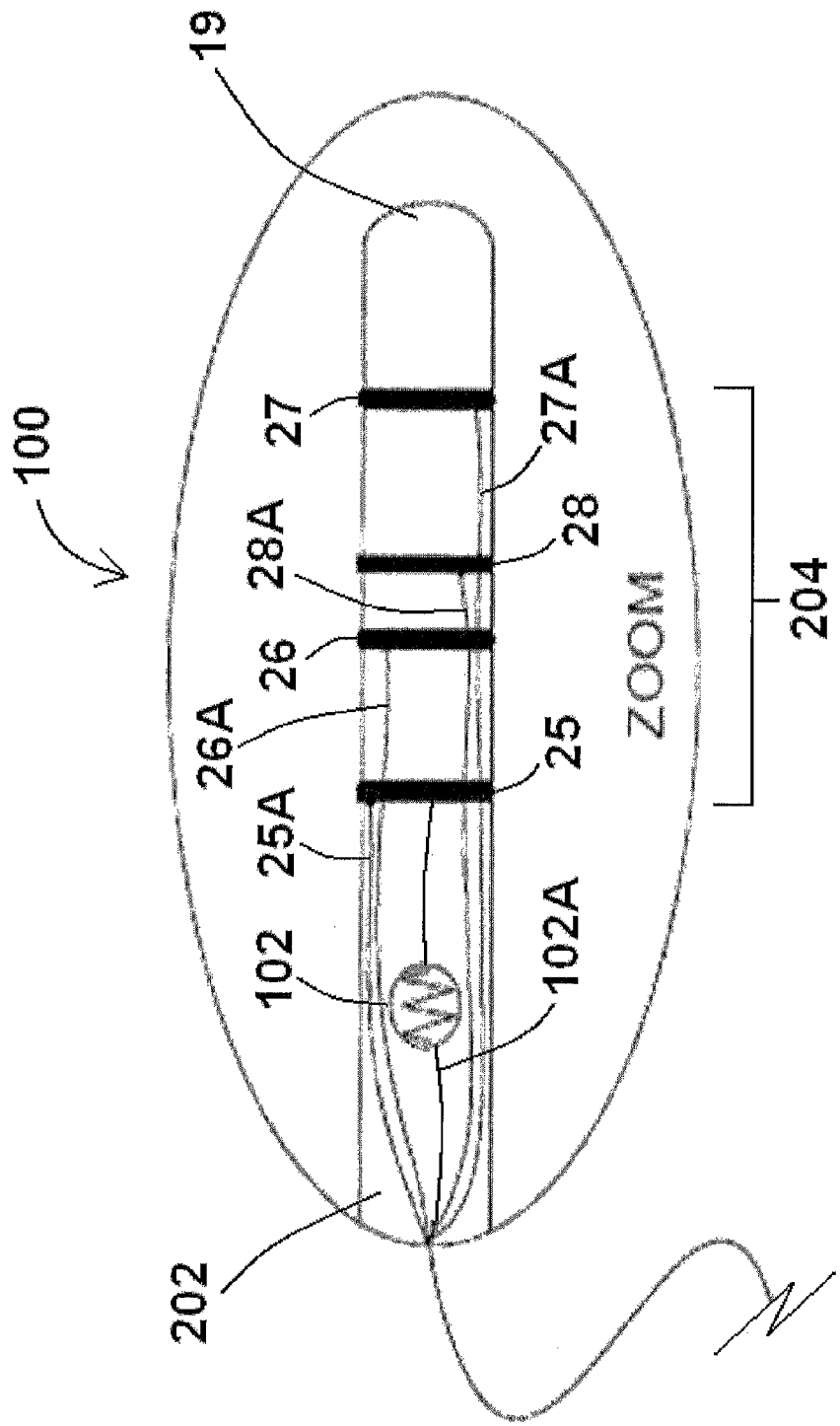

Another exemplary embodiment of at least part of an exemplary device 100 of the present disclosure is shown in FIG. 1B. As shown in FIG. 1B, device 100 comprises the same/similar arrangement of electrodes 25, 26, 27, and 28 and corresponding wires 25A, 26A, 27A, and 28A. However, in at least this exemplary embodiment, thermistor 102 shares, for example, wire 25A with excitation electrode 25, so that wire 25A provides current to excitation electrode 25 and thermistor 102. As such, and as shown in FIG. 1B, wire 102A, for example, may connect thermistor 102 to console 250 (not shown) or another portion of device 100/system 200 (as referenced herein), so transmit temperature data from thermistor 102. As wire 25A is shared between excitation electrode 25 and thermistor 102, the arrangement of electrodes and wires as shown in FIG. 1B is more efficient than the arrangement shown in FIG. 1A.

Figure 1C:
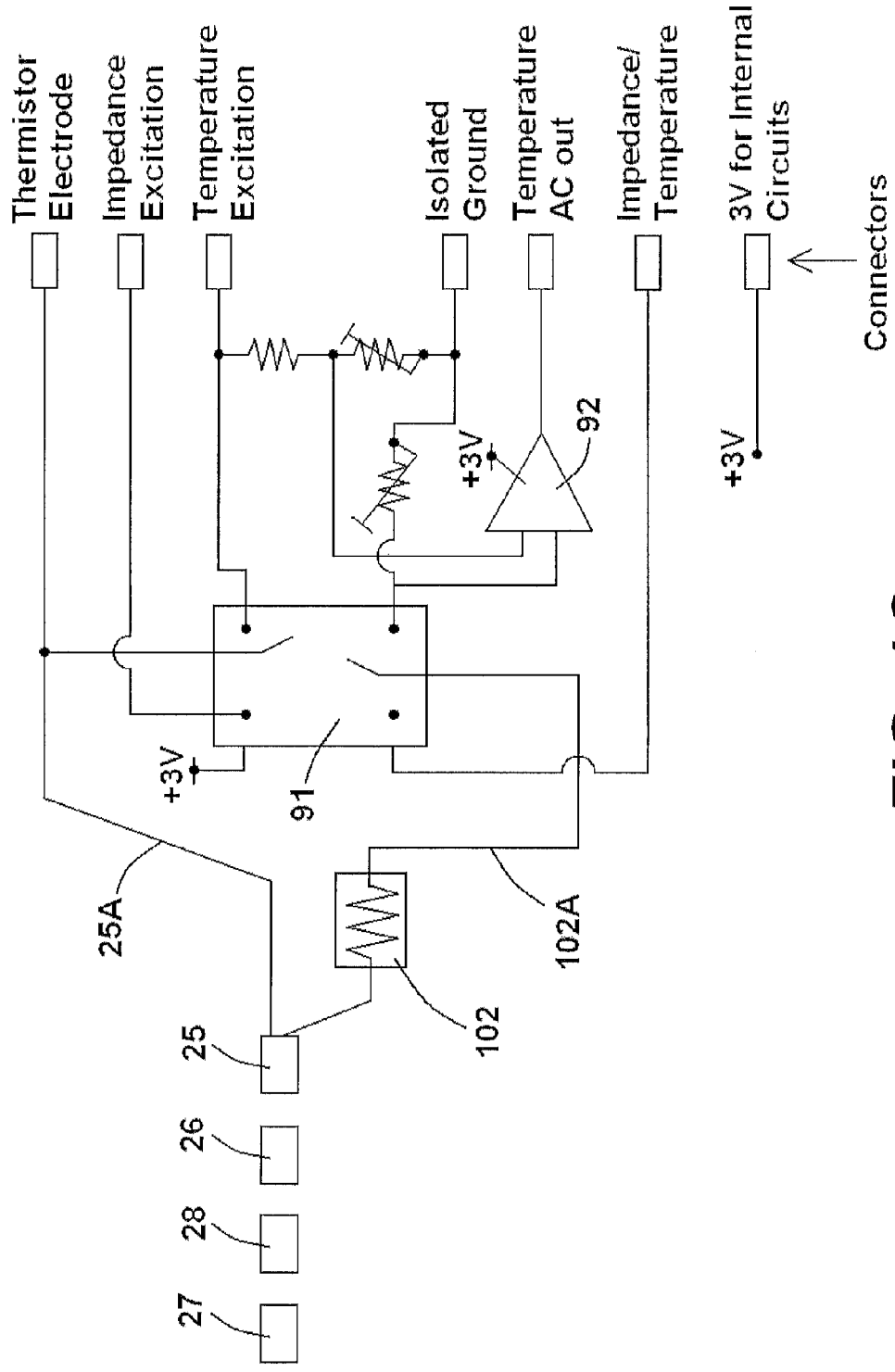
FIG. 1C shows an exemplary circuit diagram in connection with an exemplary device and/or system of the present disclosure.
Figure 1D:
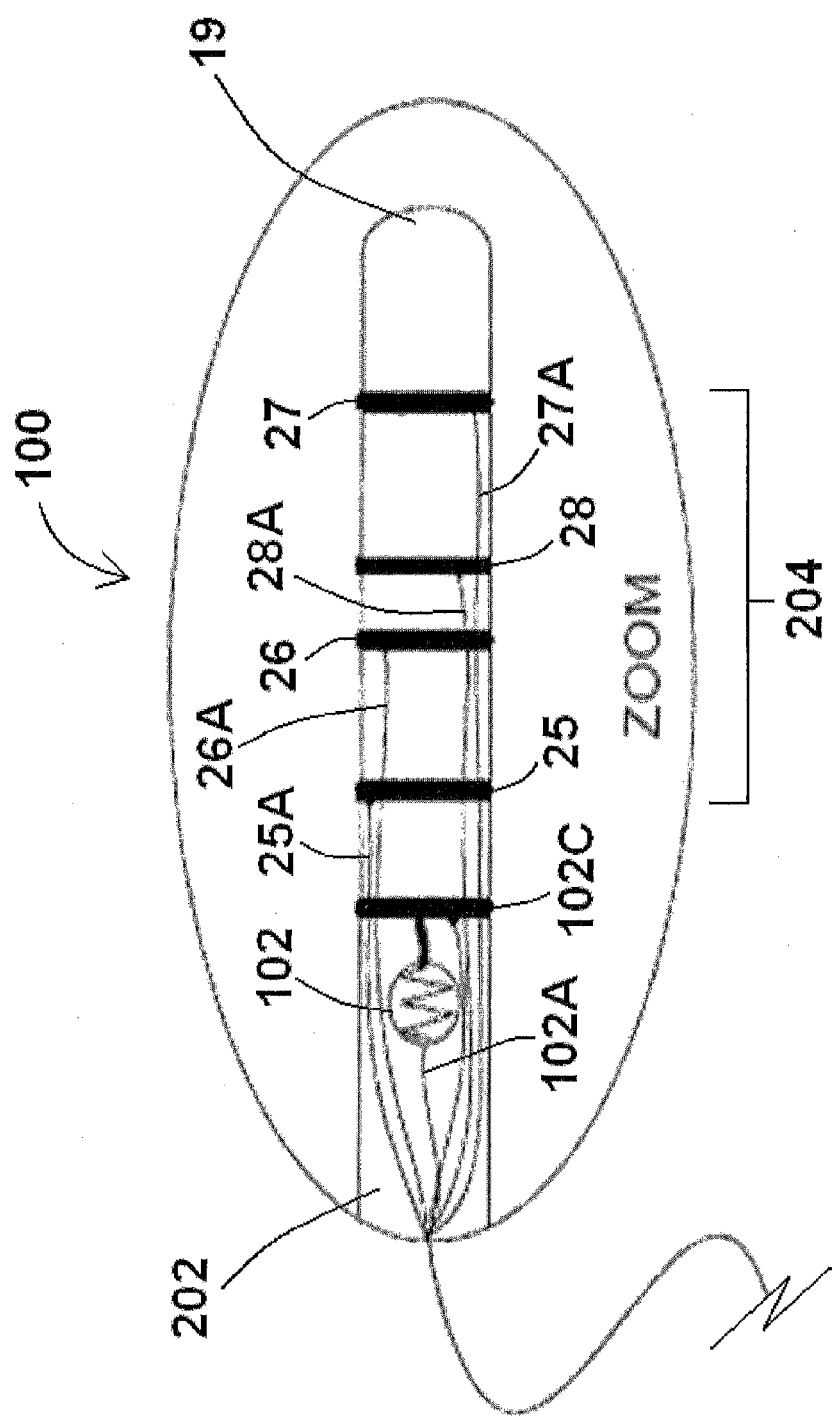
FIG. 1D shows another embodiment of at least a portion of an exemplary detection devices for obtaining parallel tissue conductance, measuring luminal cross-sectional areas, measuring fluid velocity, and/or determining plaque vulnerability using temperature within a luminal organ, said device having a thermistor, according to an embodiment of the present disclosure.

An electrical circuit diagram consistent with the arrangement of electrodes and wires shown in FIG. 1B is shown in FIG. 1C. As shown in FIG. 1C, an exemplary circuit 90 may comprise any number of components so that thermistor 102 and excitation electrode 25 and/or 27 may operate as described above. For example, and as shown in FIG. 1C, circuit 90 may comprise an analog switch 91 (such as, for example, ADG736), an amplifier 92 (such as INA333), various fixed and/or variable attenuators and wires as shown in the figure, etc., commonly found in electrical circuits. The exemplary circuit 90 shown in FIG. 1C has wiring consistent with the exemplary device 100 shown in FIG. 1B, in that wire 25A provides current to both excitation electrode 25 and thermistor 102, and wire 102A transmits temperature data from thermistor 102. An exemplary circuit 90 of the present application is not limited to the specific circuit 90 shown in FIG. 1C, which is provided as at least one example of how the various electrodes, wires, and thermistor 102 connect within an exemplary device 100/system 200.

Another exemplary embodiment of at least part of an exemplary device 100 of the present disclosure is shown in FIG. 1B. As shown in FIG. 1B, device 100 comprises the same/similar arrangement of electrodes 25, 26, 27, and 28 and corresponding wires 25A, 26A, 27A, and 28A as shown in FIG. 1B, but also includes a thermistor electrode 102C positioned near thermistor 102 along device 100. Thermistor electrode 102C, in at least one embodiment, may couple to wire 25A and 102A to provide current to thermistor 102 and provide temperature data from thermistor 102, respectively.

In at least one embodiment, thermistor 102 is positioned along elongated body 102 proximal to detector 204. When positioned in this arrangement, for example, thermistor 102 may operate to detect temperature of an injected fluid prior to detector 204 obtaining conductance data of the same injected fluid. Thermistor 102, in other embodiments, may be positioned distal to detector 204 or physically within detector 204. An exemplary thermistor 102 of the present disclosure is capable of detecting fluid native to a luminal organ as well as fluid injected into the luminal organ.

Thermistor 102, in an exemplary embodiment, may provide temperature data to a user by measuring temperature at the vicinity of thermistor 102, including, but not limited to, measuring temperature of a fluid present within a luminal organ at or near thermistor 102. As referenced herein, a luminal organ may include, but is not limited to, various bodily lumens and vessels, including blood vessels (such as coronary arteries, carotid, femoral, renal and iliac arteries), an aorta, a biliary tract, a gastrointestinal tract, a urethra, a ureter, and an esophagus.

A device 100 of the present disclosure comprising a thermistor 102 would allow thermistor 102, when positioned proximal to the various electrodes referenced herein, to detect a saline injection at the site of detector 204. For example, an exemplary thermistor 102 of the present disclosure could detect a saline injection at room temperature (approximately 20° C.) relative to body temperature (approximately 37-38° C.).

Figure 2A:
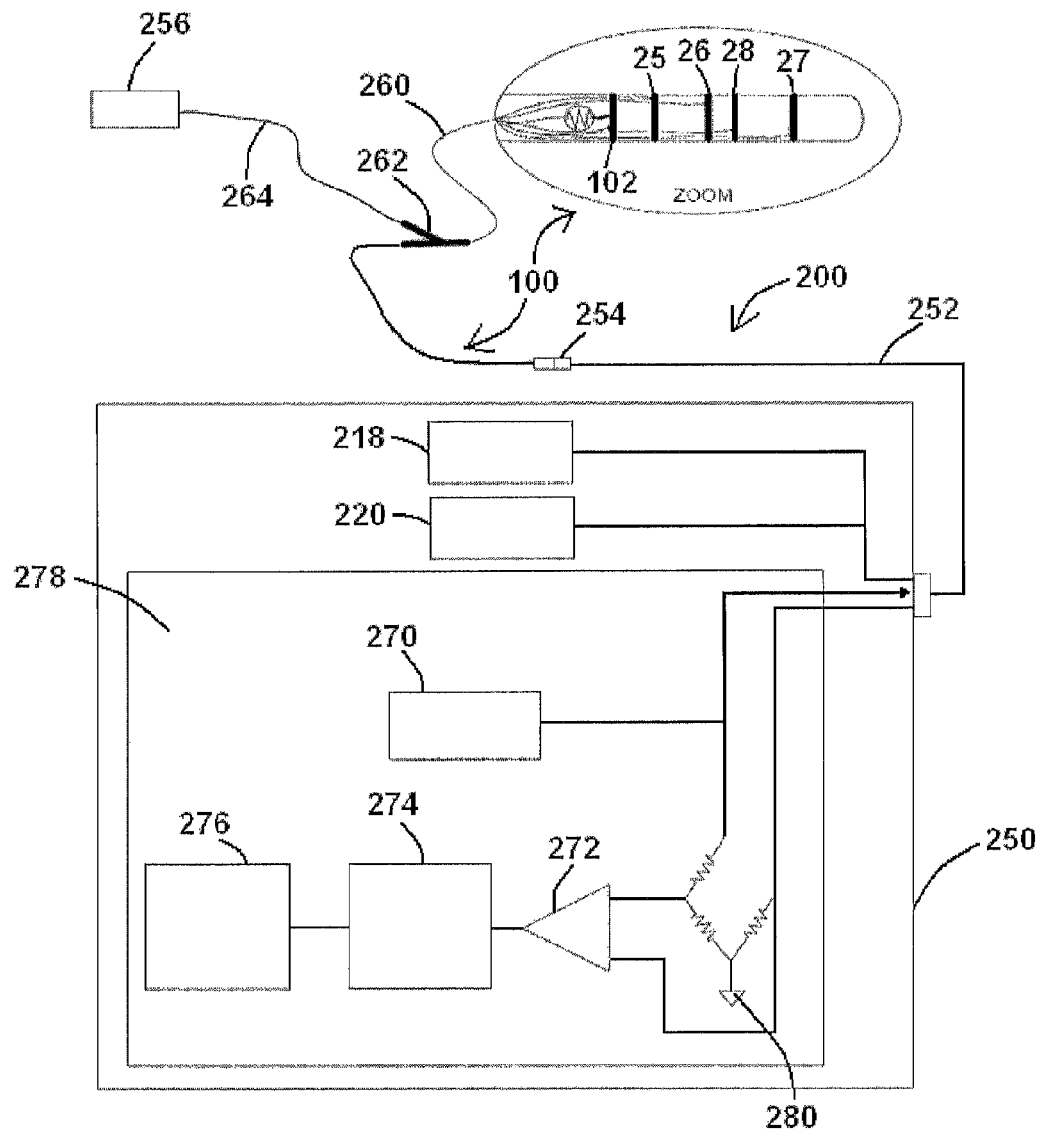
FIG. 2A shows an exemplary system for obtaining parallel tissue conductance, measuring luminal cross-sectional areas, measuring fluid velocity, and/or determining plaque vulnerability using temperature within a luminal organ, according to an embodiment of the present disclosure.

An exemplary embodiment of a system 200 obtaining parallel tissue conductance, measuring luminal cross-sectional areas, measuring fluid velocity, and/or determining plaque vulnerability using temperature of the present disclosure is shown in FIG. 2A. As shown in FIG. 2A, an exemplary system 200 comprises an exemplary device 100 of the present disclosure operatively coupled to a console 250 for controlling the operation of the various components of device 100. Device 100, as shown in FIG. 2A, has two reference arrows, one pointing to the enlarged view of the distal end of device 100, and another pointing to a portion of device 100 that is not enlarged. These two reference arrows are not pointing to different portions of an exemplary system 200, but instead are pointing to different portions of device 100.

Device 100, in at least one embodiment, may itself comprise a catheter having components as referenced above, whereby device 100 may be positioned within an engagement catheter 260 which has, for example, been inserted into a luminal organ of a patient. In another exemplary embodiment, device 100 comprises a wire having, for example, excitation electrodes 25, 27, detection electrodes 26, 28, and a thermistor 102 coupled thereto, whereby device 100 is positioned within engagement catheter 260 for use within a patient's body.

As shown in FIG. 2A, an exemplary system 200 of the present disclosure may comprise a number of connections to couple the various portions to one another. For example, and as shown in FIG. 2, console 250 may be coupled to device 100 by way of an extension cable 252 and a coupler 254. In at least another embodiment, device 100 may be coupled directly to console 250 without the use of an extension cable 252 or a coupler 254. An exemplary system 200 may also comprise an injector 256 (an exemplary solution source such as a syringe, for example) connected to engagement catheter 260 either directly via adaptor 262 or by way of an injector tube 264 positioned between injector 256 and adaptor 262. Injector 256, in at least another embodiment, may be coupled directly to the lumen of an exemplary device 100 so that the solution may be injected therethrough and through a auction/infusion port 35, 36, 37 (as described in FIGS. 2B-2G below) and into a luminal organ.

Console 250, in at least one exemplary embodiment and as shown in FIG. 2A, may comprise a thermistor excitation device 270 for the excitation/operation of thermistor 102, and an amplifier 272 for amplifying a temperature signal from thermistor 102. Console 250 may further comprise an analog signal conditioning device 274 for filtering the amplified temperature signal from amplifier 272, and a converter 276 (an analog-to-digital converter spare channel, for example) for converting the temperature signal as needed. Thermistor excitation device 270, amplifier 272, analog signal conditioning device 274, and converter 276 may be positioned upon, for example, circuit board 278 positioned within console 250, and/or each of said components may be coupled directly or indirectly to a ground 280.

System 200 may also comprise one or more components relating to the excitation of detector 204 and obtaining conductance signals therefrom. For example, system 200 may comprise a stimulator 218 (an exemplary current source) to provide a current to excite detection device 100 and/or facilitate operation of thermistor 102 (similar to a thermistor excitation device 270), and a data acquisition and processing system 220 capable of receiving conductance data from detector 204 and to process the conductance data. In at least one embodiment, data acquisition and processing system 220 is further capable of calculating a parallel tissue conductance based in part upon conductance data and a known conductivity of a solution injected into a luminal organ at or near detection electrodes 26, 28 (of, for example, detector 204). In at least another embodiment, data acquisition and processing system 220 is capable of calculating a cross-sectional area of a luminal organ based in part upon the conductance data and a known conductivity of a of a solution injected into a luminal organ at or near detection electrodes 26, 28 (of, for example, detector 204). Furthermore, an exemplary system 200 may also comprise a computer 228 for additional data processing as desired. Computer 228, in at least one embodiment, comprises a display for displaying conductance and/or temperature data, for example. In at least another embodiment, data acquisition and processing system 220 and a computer 228 are the same device, and each may perform the function of the other as referenced herein. Such a system 200 may also optionally contain signal conditioning equipment for recording of fluid flow within a luminal organ. In at least one embodiment, the impedance and pressure data are analog signals may be converted by analog-to-digital converters 230 and transmitted to computer 228 for on-line display, on-line analysis and storage. In another embodiment, all data handling is done on an entirely analog basis. Various systems 200 of the present disclosure may comprise any number of devices 100 referenced herein having one or more features and/or components as referenced herein in connection with said exemplary devices 100.

In addition, an exemplary detection device 100 of the present disclosure may comprise any number of devices 100 as shown in FIGS. 2B-2G. Referring to FIGS. 2B, 2C, 2D, and 2E, several exemplary embodiments of the detection devices 100 are illustrated. The detection devices 100 shown contain, to a varying degree, different electrodes, thermistors 102, and number and optional balloon(s). With reference to the embodiment shown in FIG. 2B, there is shown an impedance catheter 20 (an exemplary detection device 100) with four electrodes 25, 26, 27 and 28 placed close to the tip 19 of the catheter 20. A thermistor 102 is positioned proximal to electrodes 25, 26, 27, 28 to detect temperature of a fluid present in a luminal organ as referenced herein. Proximal to these electrodes is an angiography or stenting balloon 30 capable of being used for treating stenosis. Electrodes 25 and 27 are excitation electrodes, while electrodes 26 and 28 are detection electrodes, which allow measurement of cross-sectional area using detection device 100, as described in further detail herein. The portion of catheter 20 within balloon 30 includes an infusion port 35 and a pressure port 36.

Catheter 20 may also advantageously include several miniature pressure transducers 48 (as shown in FIG. 2B) carried by catheter 20 or pressure ports 36 for determining the pressure gradient proximal at the site where the CSA is measured. The pressure may be measured inside the balloon 30 and proximal, distal to and at the location of the cross-sectional area measurement, and locations proximal and distal thereto, thereby enabling the measurement of pressure recordings at the site of stenosis and also the measurement of pressure-difference along or near the stenosis. In at least one embodiment, and as shown in FIG. 2B, catheter 20 includes pressure port 90 and pressure port 91 proximal to or at the site of the cross-sectional measurement for evaluation of pressure gradients. As described below with reference to FIGS. 2H, 2I, and 2J, and in at least one embodiment, pressure ports 90, 91 are connected by respective conduits in catheter 20 to pressure sensors within system 200. Such pressure sensors are well known in the art and include, for example, fiber-optic systems, miniature strain gauges, and perfused low-compliance manometry.

In at least one embodiment, a fluid-filled silastic pressure-monitoring catheter is connected to a pressure transducer 48. Luminal pressure can be monitored by a low compliance external pressure transducer 48 coupled to the infusion channel of the catheter. Pressure transducer 48 calibration may be carried out by applying 0 and 100 mmHg of pressure by means of a hydrostatic column, for example.

In an exemplary embodiment, and shown in FIG. 2C, catheter 39 includes another set of excitation electrodes 40, 41 and detection electrodes 42, 43 located inside the angioplastic or stenting balloon 30 for accurate determination of the balloon 30 cross-sectional area during angioplasty or stent deployment. These electrodes are in addition to electrodes 25, 26, 27 and 28 and are in addition to thermistor 102.

In another exemplary embodiment, and as shown in FIG. 2G, several cross-sectional areas can be measured using an array of 5 or more electrodes. Here, the excitation electrodes 51, 52, are used to generate the current while detection electrodes 53, 54, 55, 56 and 57 are used to detect the current at their respective sites. A thermistor 102, as shown in FIG. 2G, is also present along device 100 proximal to said electrodes.

The tip of an exemplary catheter can be straight, curved or with an angle to facilitate insertion into the coronary arteries or other lumens, such as, for example, the biliary tract. The distance between the balloon 30 and the electrodes is usually small, in the 0.5-2 cm range, but can be closer or further away, depending on the particular application or treatment involved.

In at least another embodiment, and shown in FIG. 2D, catheter 21 has one or more imaging or recording device, such as, for example, ultrasound transducers 50 for cross-sectional area and wall thickness measurements. As shown in this exemplary embodiment, transducers 50 are located near the distal tip 19 of catheter 21.

FIG. 2E shows an exemplary embodiment of an impedance catheter 22 without an angioplastic or stenting balloon 30. This catheter 22 also comprises an infusion or injection port 35 located proximal relative to the excitation electrode 25 and pressure port 36.

With reference to the exemplary embodiment shown in FIG. 2F, electrodes 25, 26, 27, 28 can also be built onto a wire 18, such as, for example, a pressure wire, and inserted through a guide catheter 23 where the infusion of bolus can be made through the lumen of the guide catheter 37. A thermistor 102, as shown in FIG. 2F, can also be built onto wire 18 and be used to detect fluid temperatures.

With reference to the embodiments shown in FIGS. 2B-2G, the impedance catheter advantageously includes optional ports 35, 36, 37 for suction of contents of the organ or infusion of fluid. Suction/infusion ports 35, 36, 37 can be placed as shown with the balloon 30 or elsewhere both proximal or distal to the balloon 30 on the various catheters. The fluid inside the balloon 30 may be any biologically compatible conducting fluid. The fluid to inject through the infusion port or ports can be any biologically compatible fluid but the conductivity of the fluid is selected to be different from that of blood (e.g., saline).

In at least another embodiment (not illustrated), an exemplary catheter contains an extra channel for insertion of a guide wire to stiffen the flexible catheter during the insertion or data recording. In yet another embodiment (not illustrated), the catheter includes a sensor for measurement of the flow of fluid in the body organ.

As described below with reference to FIGS. 2H, 2I, and 2J, the excitation and detection electrodes are electrically connected to electrically conductive leads in the catheter for connecting the electrodes to the stimulator 218, for example.

FIGS. 2H and 2I illustrate two exemplary embodiments 20A and 20B of the catheter in cross-section. Each embodiment has a lumen 60 for inflating and deflating a balloon 30 and a lumen 61 for suction and infusion. The sizes of these lumens can vary in size. The impedance electrode electrical leads 70A are embedded in the material of the catheter in the embodiment in FIG. 2H, whereas the electrode electrical leads 70B are tunneled through a lumen 71 formed within the body of catheter 70B in FIG. 2I. In this exemplary embodiment, thermistor lead 75A is shown in FIG. 2H as being embedded within the catheter material, whereas thermistor lead 75B is shown as being tunneled through lumen 71 of catheter 70B.

Pressure conduits for perfusion manometry connect the pressure ports 90, 91 to transducers included in system 200. As shown in FIG. 2H, pressure conduits 95A may be formed in 20A. In another exemplary embodiment, shown in FIG. 2I, pressure conduits 95B constitute individual conduits within a tunnel 96 formed in catheter 20B. In the embodiment described above where miniature pressure transducers 48 are carried by the catheter, electrical conductors will be substituted for these pressure conduits.

Figure 2J:
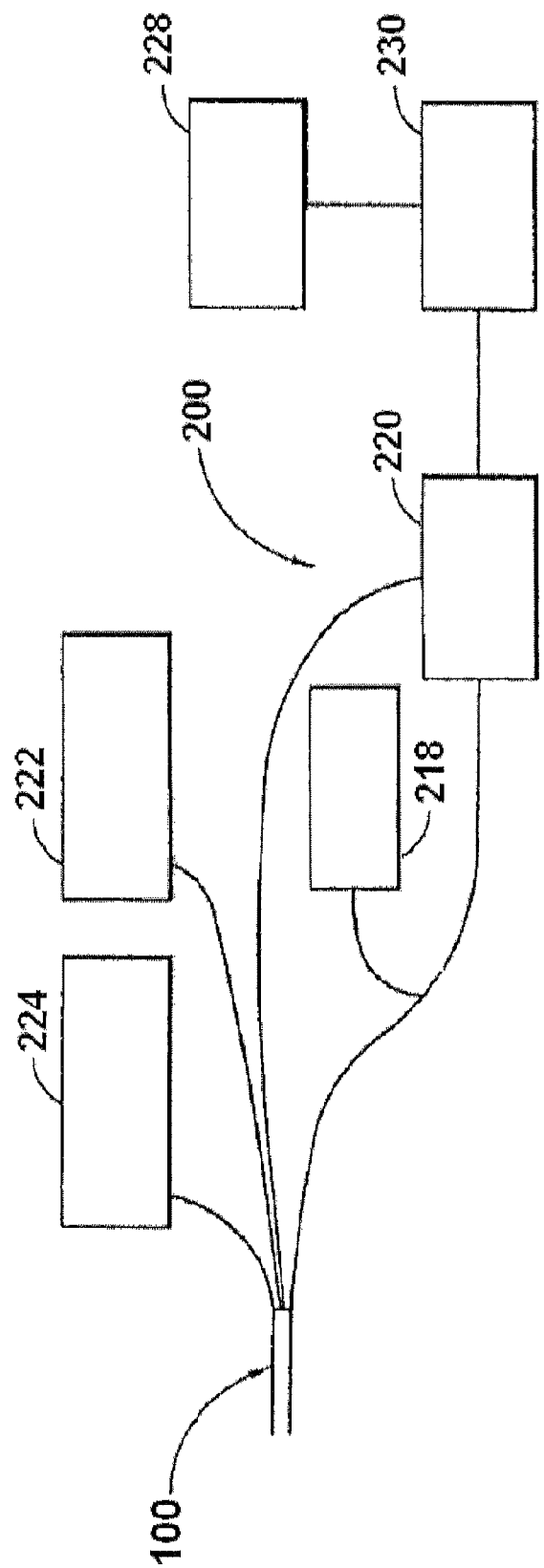
FIG. 2J shows another exemplary system for obtaining parallel tissue conductance, measuring luminal cross-sectional areas, measuring fluid velocity, and/or determining plaque vulnerability using temperature within a luminal organ, according to an embodiment of the present disclosure.

At least a portion of an exemplary system 200 for obtaining a parallel tissue conductance within a luminal organ of the present disclosure is shown in FIG. 2J. As shown in FIG. 2J, an exemplary system 200 of the present disclosure comprises a detection device 100 operably connected to a manual or automatic system 222 for distension of a balloon 30 and to a system 224 for infusion of fluid or suction of blood. In addition, and as shown in FIG. 2J, system 200 may comprise a stimulator 218 to provide a current to excite detection device 202, and a data acquisition and processing system 220 to process conductance data. Furthermore, an exemplary system 200 may also comprise a signal amplifier/conditioner (not shown) and a computer 228 for additional data processing as desired. Such a system 200 may also optionally contain signal conditioning equipment for recording of fluid flow in the luminal organ.

Figure 2K:
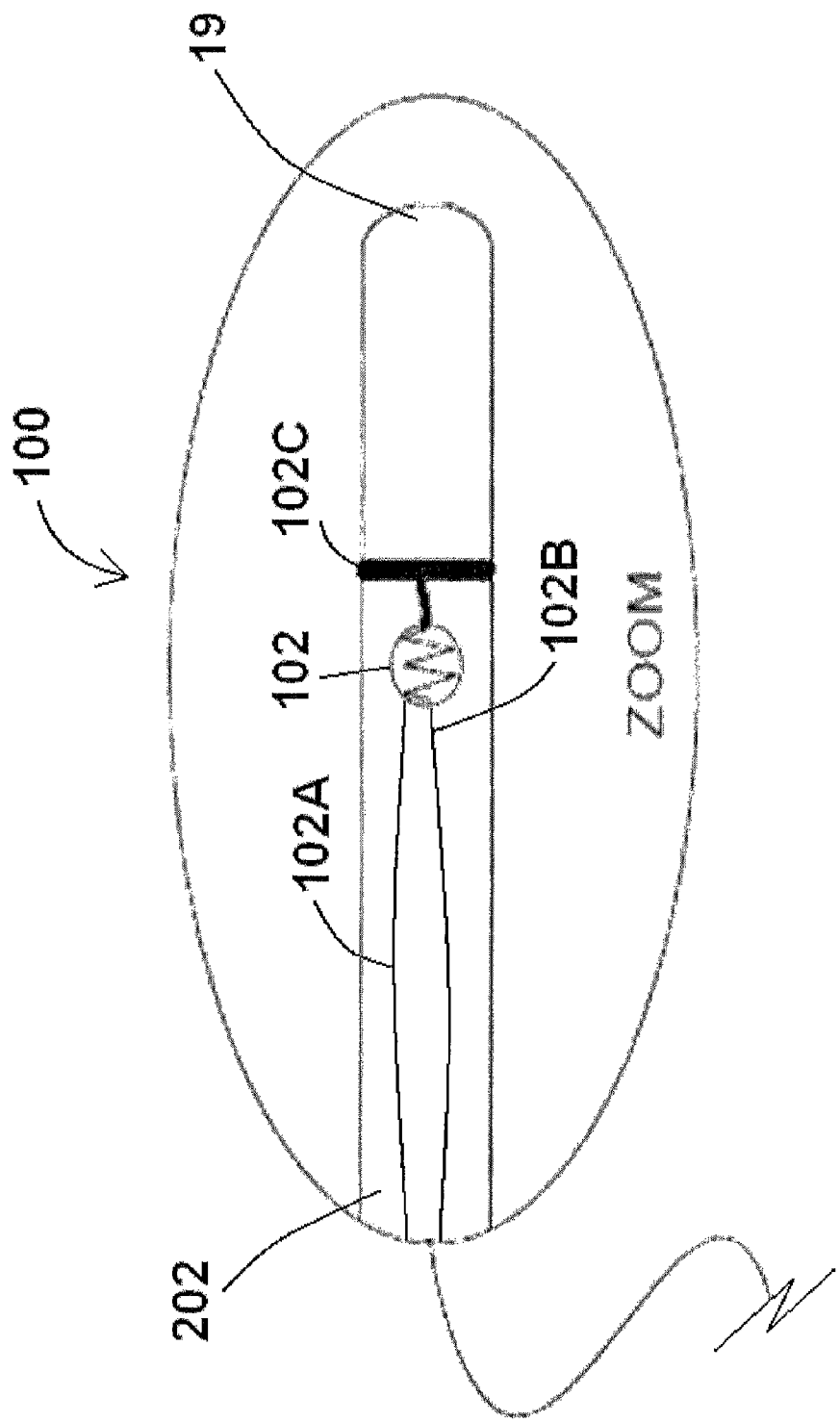
FIG. 2K shows at least a portion of an exemplary detection device for determining plaque vulnerability using temperature within a luminal organ, said device having a thermistor, according to an embodiment of the present disclosure.

At least a portion of another exemplary embodiment of a device 100 for obtaining parallel tissue conductance, measuring luminal cross-sectional areas, measuring fluid velocity, and/or determining plaque vulnerability using temperature of the present disclosure is shown in FIG. 2K. As shown in FIG. 2K, an exemplary device 100 comprises a thermistor 102 coupled thereto, whereby thermistor 102 is connected to, for example, console 250 (as shown in FIG. 2) by way of thermistor wires 102A and 102B. Thermistor wires 102A and 102B may be coupled to console 250, as referenced above, or to any number of other components of an exemplary device 100/system 200 of the present disclosure so that thermistor 102 may operate and/or provide data to user in accordance with the present disclosure. In at least one embodiment, thermistor wire 102A provides current to thermistor 102 to facilitate its operation, while thermistor wire 102B carries temperature data from thermistor 102. Any number of additional components and/or features of other devices 100 of the present disclosure may also be part of such an exemplary embodiment of a such a device 100. Thermistor 102 is shown in an enlarged view in FIG. 2K noting that, for example, device 100 may comprise any number of catheters or wires with the components referenced herein, including, but not limited to, pressure wires, guide wires, or guide catheters. Thermistor 102, in at least one embodiment, is positioned along an elongated body 202 of device 100, wherein elongated body 202 has a longitudinal axis, a proximal end (further from thermistor 102), and a distal end (closer to thermistor 102). In addition, and as shown in FIG. 2K, device 100 may also comprise a thermistor electrode 102C as described herein.

In an exemplary embodiment of a device 100 of the present disclosure, device 100 may further comprise a data acquisition and processing system 220 capable of receiving temperature data from thermistor 102. In at least one embodiment, data acquisition and processing system 220 is further capable of determining vulnerability of a plaque within a luminal organ based in part from the temperature data from thermistor 102. Such an exemplary embodiment of device 100, as referenced above, may comprise any number of other components and/or features as referenced herein in connection with various other device 100 embodiments.

In an exemplary embodiment, a system 200 is pre-calibrated and a detection device 100 is available in a package. In such an embodiment, for example, the package may also contains sterile syringes (injectors 256) with the fluid(s) to be injected. The parallel conductance, cross-sectional area, plaque vulnerability, and other relevant measures such as distensibility, tension, etc., may then typically appear on the display of computer 228. In such an embodiment, the user can then remove the stenosis by distension or by placement of a stent.

An exemplary device 100 of the present disclosure that can sense the presence of saline will have a number of advantages to make existing technologies relating to the sizing of vessels, determination of fractional flow reserves (FFRs), and plaque vulnerability determinations more reliable and robust.

Figure 3A:
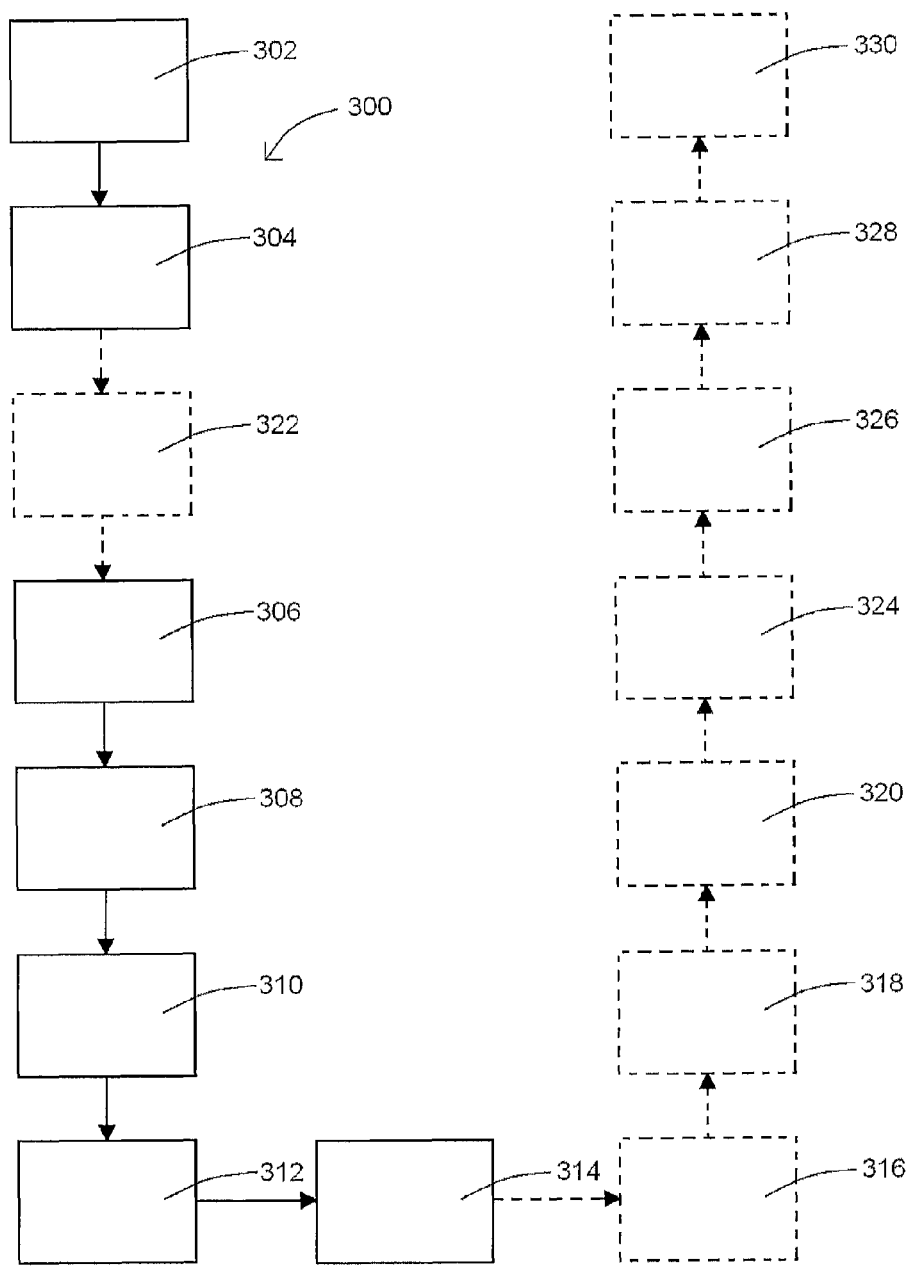
FIGS. 3A-4B show steps of exemplary methods for obtaining parallel tissue conductance, measuring luminal cross-sectional areas, measuring fluid velocity, and/or determining plaque vulnerability using temperature within a luminal organ, according to various embodiments of the present disclosure.

Steps of an exemplary method to obtain parallel tissue conductance, measure luminal cross-sectional areas, measure fluid velocity, and/or determine plaque vulnerability using temperature within a luminal organ of the present disclosure are shown in FIG. 3A. As shown in FIG. 3A, an exemplary method 300 comprises the step of introducing at least part of a detection device 100 into a luminal organ at a first location (introduction step 302), whereby, in at least one embodiment, detection device 100 comprises a detector 204 and a thermistor 102 positioned relative to the detector 204. Method 300 may further comprise the step of applying current to detection device 100 to allow detector 204 to operate (current application step 304). The application/excitation of current may be performed using a stimulator 218. Method 300, in at least one embodiment, further comprises the steps of obtaining a first temperature measurement of a fluid native to the first location, such as, for example, blood within a blood vessel (temperature measurement step 306), and injecting a solution having a known conductivity into the luminal organ at or near detector 204 of detection device 100 (solution injection step 308).

After injection of the solution, an exemplary method 300 further comprises the steps of detecting a temperature change at the first location indicative of the injected solution (temperature change detection step 310), and measuring an output conductance in connection with the injected solution based upon the detected temperature change (conductance measurement step 312). Such an exemplary method 300 may then further comprise the step of calculating a parallel tissue conductance at the first location (calculation step 314), in an exemplary embodiment, based in part upon the output conductance and the conductivity of the injected solution. Calculation step 314, in at least one embodiment, may comprise the optional step of calculating a cross-sectional area of the luminal organ at the first location.

Figure 5A:
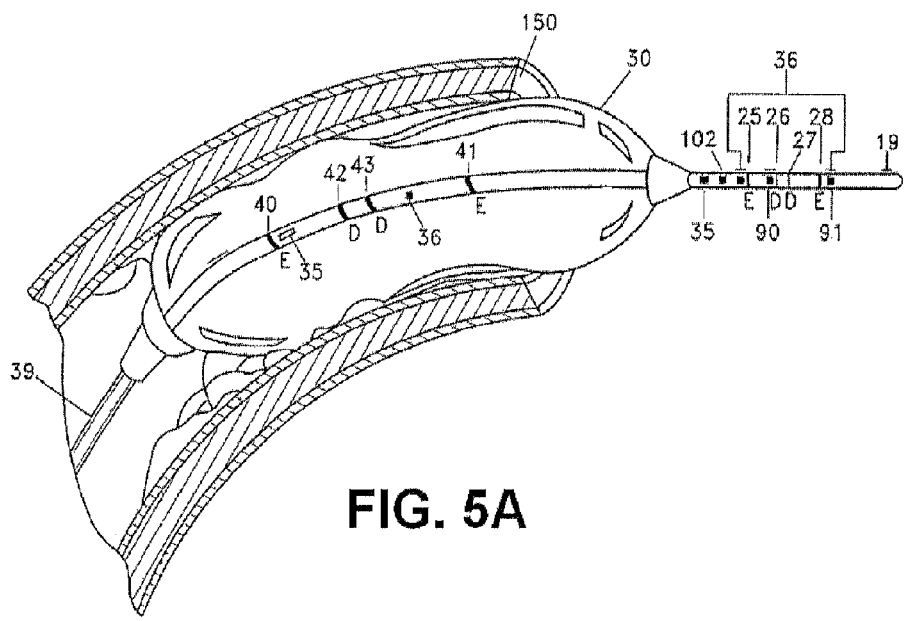
FIG. 5A shows a balloon distension of the lumen of a coronary artery according to an embodiment of the present disclosure.
Figure 5B:
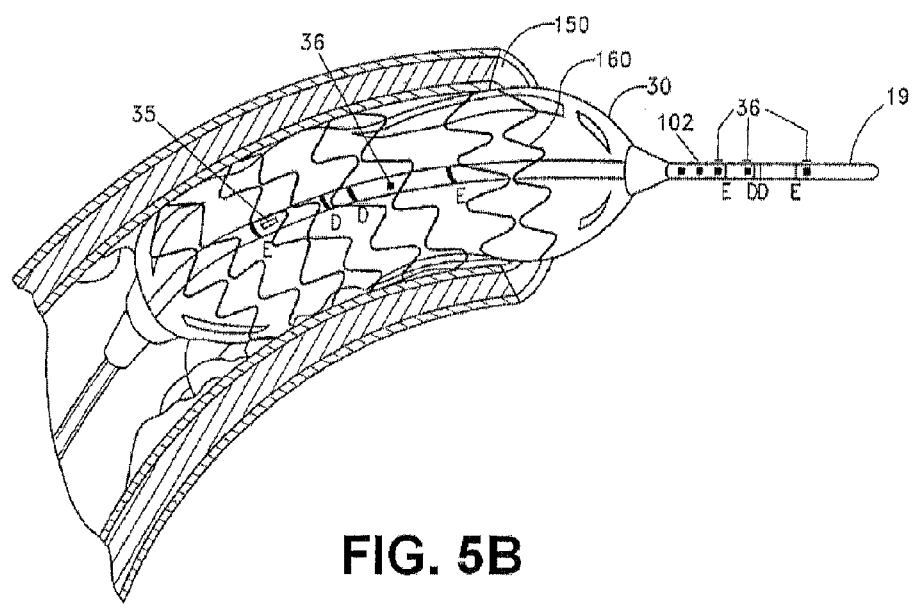
FIG. 5B shows a balloon distension of a stent into the lumen of a coronary artery according to an embodiment of the present disclosure.

In at least one exemplary method 300 of the present disclosure, method 300 further comprises the optional steps of selecting an appropriately-sized stent 160 (as shown in FIG. 5B, for example) based on the cross-sectional area at the first location (stent selection step 316), and implanting stent 160 into the luminal organ at or near the first location (a first version of a stent implantation step 318). In another exemplary embodiment, method 300 comprises the optional step of selecting a balloon catheter to be introduced into the luminal organ based upon the cross-sectional area of the luminal organ at the first location (a first version of catheter selection step 320).

As used within the various methods 300 of the present disclosure, detector 204 of device 100 may comprise two detection electrodes positioned in between two excitation electrodes, wherein the two excitation electrodes are capable of producing an electrical field. In an exemplary conductance measurement step 312, for example, conductance measurement step 312 is performed using the detection device 100.

In at least one exemplary method 300 of the present disclosure, temperature measurement step 306 is performed using the thermistor. In an exemplary embodiment, the fluid native to the first location comprises blood, and wherein the injected solution comprises saline. In another exemplary method 300, temperature measurement step 306 comprises obtaining multiple temperature measurements of the fluid native to the first location over time and displaying the multiple temperature measurements on a display (computer 228). In an additional method 300, temperature change detection step 310 comprises obtaining additional temperature measurements and displaying the additional temperature measurements on the display (computer 228).

In an exemplary method 300 of the present disclosure, method 300 further comprises the optional step of obtaining a native conductance in connection with the native fluid prior to the step of injecting a solution (native conductance measurement step 322). In such a method 300, for example, native conductance measurement step 322 may comprise obtaining multiple native conductances, and conductance measurement step 312 may comprise obtaining multiple output conductances. In at least one embodiment, the multiple native conductances and the multiple output conductances are displayed on a display (computer 228). As shown in FIG. 3A, optional native conductance measurement step 322 may be performed directly after current application step 304, for example, or may be performed before or after any number of the steps referenced within FIG. 3A.

Detecting temperature change, as referenced above, may be indicative of the presence of an injected solution at the location of, for example, thermistor 102 when device 100 is positioned within a luminal organ. In at least one embodiment, such a temperature change may be at least 5° C. lower than the first temperature measurement. In an exemplary embodiment of a method 300 of the present disclosure, solution injection step 308 temporarily substantially displaces the blood at the first location. Furthermore, and in at least one embodiment, conductance measurement step 312 may include measuring multiple output conductances until the temperature within the luminal organ reaches a threshold temperature. In at least one embodiment, the threshold temperature is within about 2° C. of the first/native temperature measurement, and in other embodiments, the threshold temperature could be any number of temperatures including and between the lowest and highest detected temperatures.

In at least one embodiment, an optimal output conductance is obtained by averaging the multiple output conductances. In another embodiment, the output conductance having a largest or smallest value within the multiple output conductances is deemed an optimal output conductance. As shown above, a user has many options for determining which conductance values to use, as those conductance values obtained between the time of detecting a temperature change and the threshold temperature would be indicative of a successful saline injection.

An exemplary detection device 100 used in connection with an exemplary method 300 of the present disclosure may further comprise an inflatable balloon 30 along a longitudinal axis of the detection device 100. With such a device 100, for example, method 300 may further comprise the optional step of inflating balloon 30 to breakup materials causing stenosis at the first location (a first version of a balloon inflation step 324). Furthermore, and in at least one embodiment, detection 100 may further comprise a stent 160 (as shown in FIG. 5B, for example), located over the balloon 30, wherein stent 160 is capable of being distended to a desired lumen size and implanted into the luminal organ at or near the first location. With such a device 100, for example, method 300 may further comprise the optional steps of distending stent 160 by inflating balloon 30 (another version of balloon inflation step 324), and releasing and implanting stent 160 into the luminal organ at or near the first location (a second version of a stent implantation step 318). As referenced above, the various method steps may be performed in the order as shown in FIG. 3A, but are not limited to being performed in such an order. For example, when positioning a stent 160, stent implantation step 318 may be performed without balloon inflation step 324 or may be performed after balloon inflation step 324.

In at least an additional embodiment of a method 300 of the present disclosure, detection device 100 further comprises a pressure transducer 48 (as shown in FIG. 2B). Using such a device 100, for example, method 300 may further comprise the optional steps of measuring a first pressure gradient value from the pressure transducer at or near the first location (pressure gradient measurement step 326) and calculating a cross-sectional area of the treatment site based in part on the parallel tissue conductance and the first pressure gradient value (calculation step 314).

In at least another embodiment of a method 300 of the present disclosure, method 300 further comprises the optional step of calculating a first nodal voltage and a first electrical field based on the out conductance and a first current density (first nodal voltage calculation step 328). In such an embodiment, method 300 may further comprise the optional steps of applying finite element analysis to the first nodal voltage and first electrical field values (finite element analysis application step 330), determining appropriate catheter dimensions for minimizing nonparallel electrical field lines at the first location (catheter dimension determination step 332), and selecting an appropriately-sized catheter for introduction into the luminal organ at or near the first location (a second version of catheter selection step 320). In at least one embodiment, finite element analysis application step 330 is performed using a finite element software package.

Figure 3B:
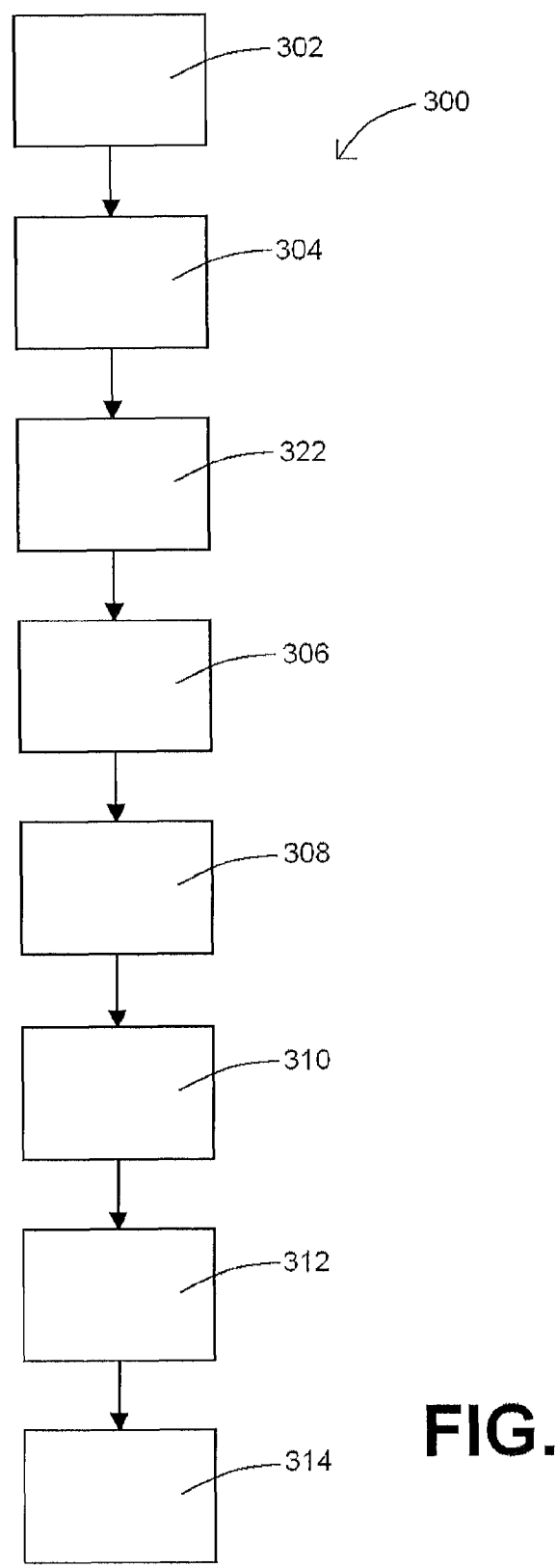

In at least another exemplary method 300 of the present disclosure, and as shown in FIG. 3B, method 300 comprises introduction step 302, current application step 304, native conductance measurement step 322, temperature measurement step 306, solution injection step 308, temperature change detection step 310, conductance measurement step 312, and calculation step 314. In at least one embodiment, calculation step 314 comprises the optional step of calculating a cross-sectional area of the luminal organ at the first location.

Figure 3C:
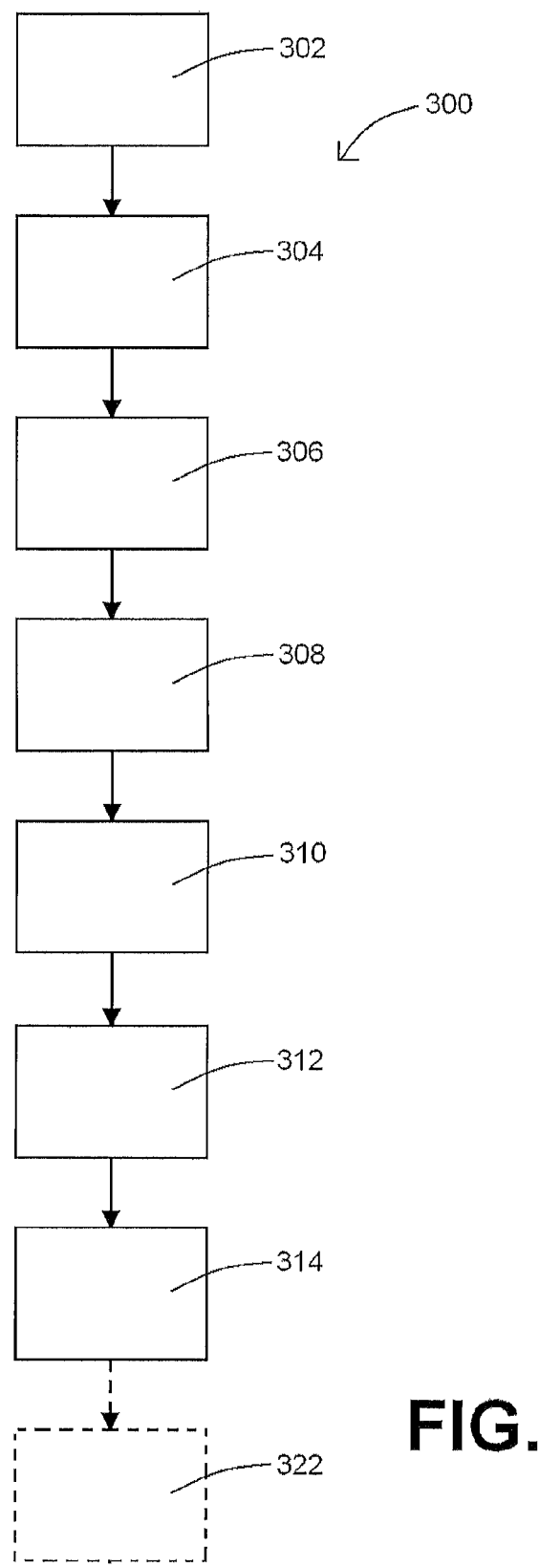

In yet another exemplary method 300 of the present disclosure, and as shown in FIG. 3C, method 300 comprises introduction step 302, current application step 304, temperature measurement step 306, solution injection step 308, temperature change detection step 310, conductance measurement step 312, and, calculation step 314, wherein calculation step comprises calculating a cross-sectional area of the luminal organ at the first location based in part upon the output conductance and the conductivity of the injected solution. Such a method 300, in at least one embodiment, may further comprise the optional step of selecting a balloon catheter to be introduced into the luminal organ based upon the cross-sectional area of the luminal organ at the first location (a first version of catheter selection step 320).

Figure 4A:
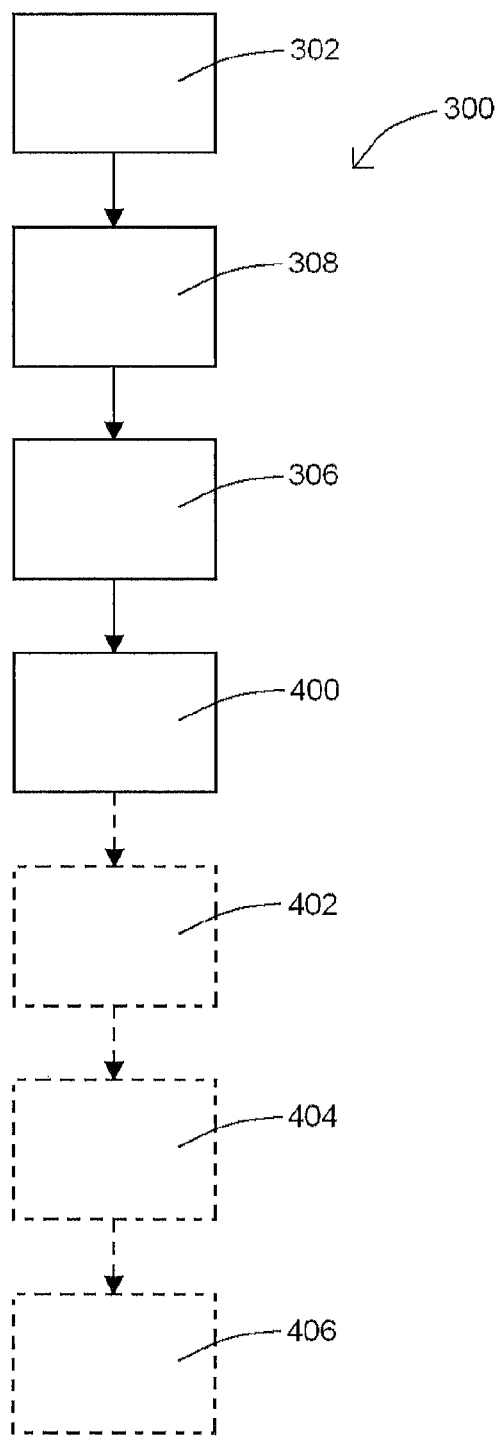

Steps of another exemplary method 300 to obtain parallel tissue conductance, measure luminal cross-sectional areas, measure fluid velocity, and/or determine plaque vulnerability using temperature within a luminal organ of the present disclosure are shown in FIG. 4A. As shown in FIG. 4A, an exemplary method 300 comprises the steps of introducing at least part of a detection device into a luminal organ at a plaque site, the detection device having a thermistor (a version of introduction step 302), injecting a solution into the luminal organ at or near the thermistor of the detection device (a version of solution injection step 308), and detecting a first temperature measurement at the plaque site indicative of a plaque and the injected solution (a version of temperature measurement step 306). Such an exemplary method 300 may further comprise the step of determining vulnerability of a plaque at the plaque site based in part upon the first temperature at the plaque site (plaque vulnerability determination step 400).

In at least one exemplary embodiment, temperature measurement step 306 is performed using the thermistor. In another exemplary embodiment of method 300, the injected solution comprises saline. In at least another exemplary embodiment of a method 300 of the present disclosure, temperature measurement step 306 comprises detecting multiple temperature measurements at the plaque site over time and displaying the multiple temperature measurements on a display.

In an exemplary method 300 of the present disclosure, and as shown in FIG. 4A, method 300 comprises the optional steps of moving the detection device within the luminal organ to a plaque-free location (device movement step 402), injecting additional solution into the luminal organ at or near the thermistor of the detection device (additional solution injection step 404), and detecting a second temperature measurement at the plaque-free location indicative of the injected solution (second temperature detection step 406).

In at least one embodiment of a plaque vulnerability determination step 400 of an exemplary method 300 of the present disclosure, plaque vulnerability determination step 400 is further based upon a difference between the first temperature measurement and the second temperature measurement. In such an embodiment, a plaque may be determined to be less vulnerable of the difference between the first temperature measurement and the second temperature measurement is zero to relatively low, and the plaque may be determined to be more vulnerable of the difference between the first temperature measurement and the second temperature measurement is relatively high. In at least one embodiment, the plaque may be determined to be vulnerable if the difference between the first temperature measurement and the second temperature measurement is about 1° C. Any number of additional steps of an exemplary method 300 of the present disclosure may also apply to the method 300 shown in FIG. 4A, as well as any other depiction of an exemplary method 300 of the present disclosure.

Figure 4B:
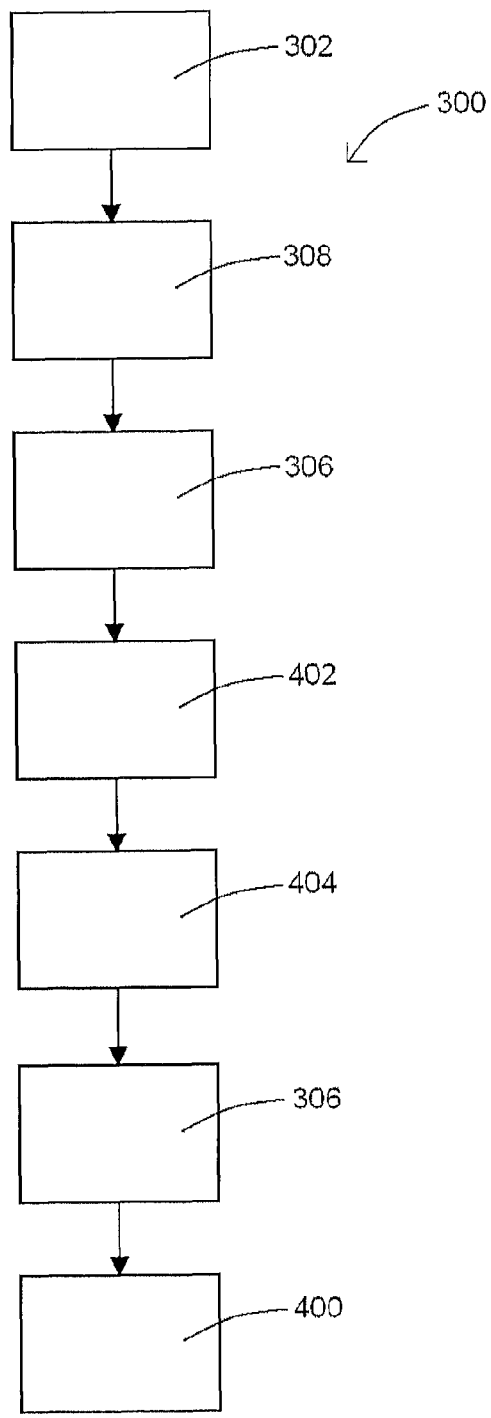

In at least another method 300 of the present disclosure, and as shown in FIG. 4B, method 300 comprises introduction step 302, solution injection step 308, temperature measurement step 306, device movement step 402, additional solution injection step 404, a second temperature measurement step 306, and the step of determining vulnerability of a plaque based upon a difference between a first temperature measurement and a second temperature measurement (a version of plaque vulnerability determination step 400). Using such a method 300, for example, device movement step 402 may be to move the device 100 from a plaque site to a plaque-free site, or may be to move the device 100 from a plaque-free site to a plaque site.

In at least one embodiment, the two temperature measurement steps 306 are performed using a thermistor 102. In at least another embodiment, the first temperature measurement step 306 comprises detecting multiple temperature measurements at the first location over time, and the second temperature measurement step 306 comprises detecting multiple temperature measurements at the second location over time and displaying the multiple temperature measurements on a display. In at least one exemplary embodiment of a method 300 of the present disclosure, the first temperature measurement and the second temperature measurement (from the two temperature measurement steps 306) are further indicative of luminal organ tissue.

Referring to the embodiment of an exemplary device 100 of the present disclosure shown in FIG. 5A, the angioplasty balloon 30 is selected on the basis of $G_p$ (and/or a direct cross-sectional area determination, for example) and is shown distended within a coronary artery 150 for the treatment of stenosis. As described above with reference to FIG. 2C, a set of excitation electrodes 40, 41 and a set of detection electrodes 42, 43 are located within the angioplasty balloon 30. In another embodiment, and as shown in FIG. 5B, an angioplasty balloon 30 is used to distend a stent 160 within blood vessel 150. As shown in FIGS. 5A and 5B, such exemplary devices 100 comprise a thermistor 102 coupled thereto as referenced herein in connection with various other device 100 embodiments, whereby thermistor 102 is operable to detect fluid temperatures as referenced herein.

CSA and Gp

A two injection method allowing for the simultaneous determination of cross-sectional area (CSA) and parallel conductance ($G_p$) of luminal organs are currently known in the art by way of U.S. Pat. No. 7,454,244 to Kassab. As referenced therein, each injection provides a known conductivity-conductance (σ-G) relation or equation as per an Ohm's law modification that accounts for parallel conductance (namely current losses from the lumen of vessel):

$$G = (CSA/L)\sigma + G_p \quad [1]$$

wherein G is the total conductance, CSA is the cross-sectional area of the luminal organ (which may include, but is not limited to, various bodily lumens and vessels, including blood vessels, a biliary tract, a urethra, and an esophagus, for example), L is a constant for the length of spacing between detection electrodes of the detection device used, σ is the specific electrical conductivity of the fluid, and $G_p$ is the parallel conductance (namely the effective conductance of the structure outside of the fluid).

The physical principle for sizing of vessel is based on an Ohm-type law which uses saline to calibrate the vessel size relative to known phantom dimensions. The issue arises as to when a system 200 of the present disclosure can sense the presence of saline in order to measure the saline conductance whose conductivity is known (unlike blood, whose conductivity is not precisely known and varies in different patients and under different conditions based upon, for example, hematocrit, shear rate, and blood cell orientation). The conductance of saline may deflect up, down or remain the same depending on weather it is more conductive, less conductive or of same conductivity as that of blood. Since this may vary in different patients depending on their blood properties, composition, etc., it is beneficial to have an independent sensor to denote the presence of saline.

Equation [1], and derivations and/or related equations thereto comprising CSA and Gp, are both temperature dependent as they are functions of conductance and conductivity. Each 1° C. change in temperature can cause a 1% change in conductance or conductivity. For example, if a user of a device 100/system 200 of the present disclosure believe that conductance measurements are being made within a body at 37° C., but such measurements are actually being made at 27° C. due to the lower temperature of a saline injection, for example, those conductance measurements could be incorrect by approximately 10% or more. If those incorrect measurements are then used to determine an appropriately-sized stent, such a stent could either be too large or too small for that particular vessel.

By knowing the temperature at the time/location of injection, one can then determine the linear relationship between conductivity and temperature. For example, and as referenced herein, using a device 100/system 200 of the present disclosure would allow a user to know the temperature of the injected bolus at the time the conductance measurements are taken, as a thermistor 102 can provide one or more temperature measurements to the user before, during, and/or after the bolus injection itself.

Calibration of such a device 100/system 200, for example, may be made using phantoms (tubes with known diameters) are referenced herein. To obtain a known calibration range, one could use a device 100/system 200 of the present disclosure to "size" the phantom, for example, at various increments between 20° C. and 40° C. For example, a phantom could be placed within a 0.9% saline (normal) or 0.45% saline (half-normal) bath at 20° C., and device 100 could be used to obtain conductance measurements. The bath could then be warmed to 22° C., for example, and additional measurements could be obtained. Additional measurements at 24° C., 26° C., etc., up to 40° C. could be made, and that calibration data could be programmed into system 200, for example, so that the most accurate conductance measurements could then be made within a vessel of an unknown diameter, such as within a mammalian bodily vessel/luminal organ. Therefore, when a user knows the bolus temperature, the user can match conductivity to temperature to obtain the most accurate readings.

Automation of Sizing and Fluid Velocity Measurements

Figure 6:
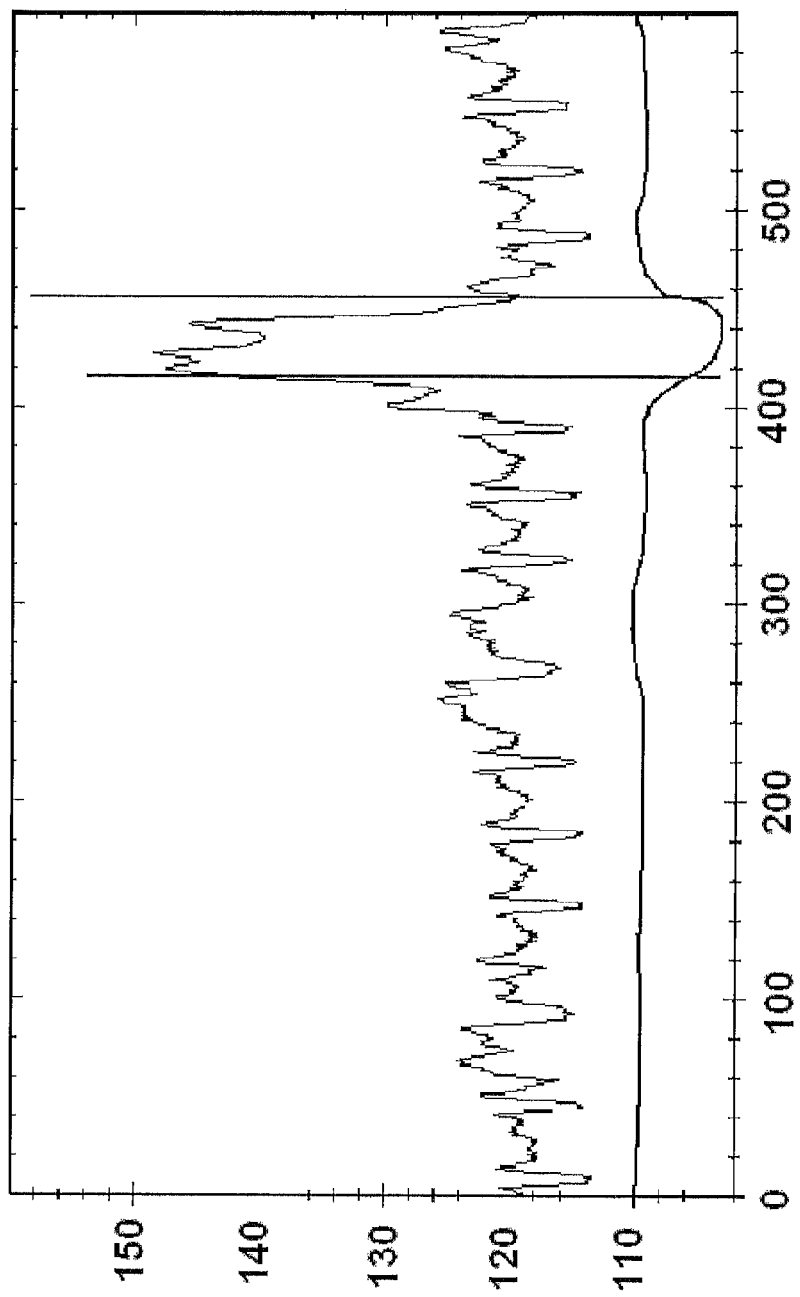
FIG. 6 shows a graph demonstrating the use of an exemplary device and/or system of the present disclosure.

FIG. 6 shows a graph demonstrating the use of an exemplary device 100/system 200 of the present disclosure. Two data lines are shown in FIG. 6, namely an upper line representing the conductivity of fluid detected by a detector 204 of a device 100 of the present disclosure over time, and a lower line representing temperature over time as detected by a thermistor 102 of a device 100 of the present disclosure. As shown in FIG. 6, the upper line remains relatively constant over time, and then deflects upwards for a period of time, eventually falling back to its original constant level. This upward deflection is indicative of the detection of saline that is more conductive than a particular patient's blood, resulting in a temporary upward deflection at the time the saline is detected by device 100. In this instance, the temperature (lower line) shows a clear downward deflection, a slight plateau, and is followed by recovery of temperature when the blood washes out the saline. The plateau represents unmixed saline and hence conductance measurement at this instant of time is preferred.

The beginning of such a measurement, for example, can be triggered by a threshold drop in temperature such as a 5° C. drop relative to the baseline temperature. The end of measurement (to define an interval for preferred detection) can be triggered by the recovery of the detected temperature to the baseline, such as within 2° C. of the baseline. Within this interval, the conductance measurement (used for sizing, fractional flow reserve, plaque vulnerability and/or plaque-type determination, etc.) can be made, at the minimum plateau of temperature.

For a fluid velocity determination, for example, one may look immediately to the right of first trigger to obtain the conductance-time deflection curve. If the thresholds are not realized, due to a bad injection (when the catheter not engaged into the artery) or substantial mixing of saline and blood (from too slow of an injection), no measurement will be provided by the device 100/system 200 and the operator can then repeat the injection in attempt to obtain a suitable measurement.

Figure 7:
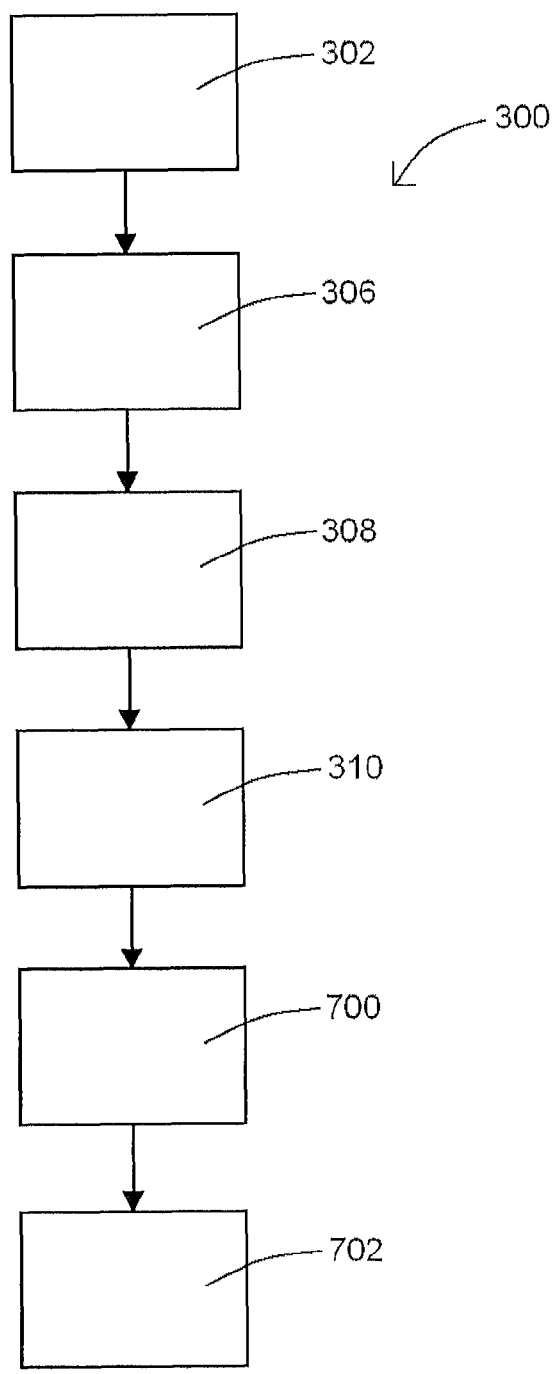
FIG. 7 shows steps of an exemplary method for obtaining parallel tissue conductance, measuring luminal cross-sectional areas, measuring fluid velocity, and/or determining plaque vulnerability using temperature within a luminal organ, according to an embodiment of the present disclosure.

Consistent with the foregoing, steps of an exemplary method 300 to obtain parallel tissue conductance, measure luminal cross-sectional areas, measure fluid velocity, and/or determine plaque vulnerability using temperature within a luminal organ of the present disclosure are shown in FIG. 7. As shown in FIG. 7, an exemplary method 300 comprises introducing at least part of a detection device into a luminal organ at a first location wherein the detection device has a thermistor (a version of introduction step 302), obtaining a first temperature measurement indicative of a fluid native to the first location (a version of temperature measurement step 306), injecting a solution into the luminal organ at a known distance from the thermistor of the detection device (a version of solution injection step 308), and detecting a temperature change at the first location indicative of the injected solution (a version of temperature change detection step 310). Such an exemplary method 300 may also comprise the steps of calculating the time from injecting the solution to detecting the temperature change at the first location (time calculation step 700), and calculating fluid velocity at the first location based in part upon calculated time and the known distance from the injection to the thermistor (fluid velocity calculation step 702). As referenced herein, any number of other method 300 steps, as well as any number of devices 100 and/or systems 200 of the present disclosure may be used in connection with the aforementioned exemplary method 300.

The integrity of the injection can also be assessed, with feedback provided to the operator/physician. The degree of deflection, in at least one embodiment, can be used to make this assessment. For example, an injection made at 20° C. (room temperature) through the catheter is expected to increase in temperature (heat up) by couple of degrees at the site of coronary artery. Hence, a deflection to 25° C., for example, can be used to accept the measurement. If the deflection is only to 30° C., which is still large enough to trigger the measurement, the measurement will be rejected and the operator may then decide to repeat the injection. Therefore, a visual display of the temperature changes along with system 200 instructions to the user would help ensure the integrity of the injections and the corresponding output measurements. It is noted that conductance measurements triggered by temperature will detect upward deflection, downward deflection, or no deflection regardless of the relative conductance of saline to blood.

Since the conductivity values for saline are temperature-dependent (for example, an 0.5-1.0° C. increase in temperature resulting in a higher conductivity), an accurate determination of temperature will allow the correct values of conductivities to be used given that a linear relation exists between temperature and conductivity. This will provide a more accurate measurement of CSA given its direct relation with conductivity. The linear relation between conductivity and temperature will allow an exemplary system 200 of the present disclosure to assign the correct conductivity depending on the recorded temperature of saline at the site of measurement.

Detection of Vulnerable Plaque

It is known that a vulnerable plaque that may be susceptible to rupture is an active inflammation with a locally higher temperature (e.g., within a degree higher than surrounding tissue/blood). Previous attempts made at measuring the temperature of a lesion to determine vulnerability have encountered the following difficulty. A plaque (even intermediate disease or stenosis) can produce local flow disturbances which can lead to viscous dissipation due to viscosity of blood. The energy dissipation translates into thermal heat (i.e., a slight increase in temperature, within 1° C.) in the vicinity of the stenotic lesion. Hence, a rise in temperature in the vicinity of lesion may be due to the flow disturbance energy dissipation regardless of plaque temperature.

To correct for this potential incorrect determination, the disclosure of the present application discloses the measurement of temperature using a thermistor 102 positioned along a device 100 of the present disclosure at the plaque site during the saline injection, as opposed to an attempted temperature measurement in the presence of blood as with previous attempts. The rationale is that saline has approximately one fourth the viscosity of blood and therefore will lead to far less viscous dissipation (roughly one fourth) which can prevent the "noise" of previous measurements. This will allow the present system to detect largely the temperature of the lesion as opposed to nearby hemodynamic disturbances during the saline injection.

To consider a method of measuring parallel conductance ($G_p$) and related impedance, which are used to determine CSA or evaluate the type and/or composition of a plaque, a number of approaches may be used. In one approach, luminal cross-sectional area is measured by introducing a catheter from an exteriorly accessible opening (e.g., mouth, nose or anus for GI applications; or e.g., mouth or nose for airway applications) into the hollow system or targeted luminal organ. In an exemplary approach, $G_p$ is measured by introducing a catheter from an exteriorly accessible opening into the hollow system or targeted luminal organ. For cardiovascular applications, the catheter can be inserted into the organs in various ways, for example, similar to conventional angioplasty. In at least one embodiment, an 18 gauge needle is inserted into the femoral artery followed by an introducer, and a guide wire is then inserted into the introducer and advanced into the lumen of the femoral artery. A 4 or 5 Fr conductance catheter is then inserted into the femoral artery via wire and the wire is subsequently retracted. The catheter tip containing the conductance (excitation) electrodes can then be advanced to the region of interest by use of x-ray (using fluoroscopy, for example). In another approach, this methodology is used on small to medium size vessels, such as femoral, coronary, carotid, and iliac arteries, for example.

With respect to the solution injection, studies indicate that an infusion rate of approximately 1 ml/s for a five second interval is sufficient to displace the blood volume and results in a local pressure increase of less than 10 mmHg in the coronary artery. This pressure change depends on the injection rate, which should be comparable to the organ flow rate. In at least one approach, dextran, albumin or another large molecular weight molecule can be added to the solution (saline, for example) to maintain the colloid osmotic pressure of the solution to reduce or prevent fluid or ion exchange through the vessel wall.

In an exemplary approach, a sheath is inserted either through the femoral or carotid artery in the direction of flow. To access the left anterior descending (LAD) artery, the sheath is inserted through the ascending aorta. For the carotid artery, where the diameter is typically on the order of 5.0-5.5 mm, a catheter having a diameter of 1.9 mm can be used. For the femoral and coronary arteries, where the diameter is typically in the range from 3.5-4.0 mm, a catheter of about 0.8 mm diameter would be appropriate. Such a device can be inserted into the femoral, carotid or LAD artery through a sheath appropriate for the particular treatment. Measurements for all three vessels can be similarly made.

The saline solution can be injected by hand or by using a mechanical injector to momentarily displace the entire volume of blood or bodily fluid in the vessel segment of interest. The pressure generated by the injection will not only displace the blood in the antegrade direction (in the direction of blood flow) but also in the retrograde direction (momentarily push the blood backwards). In other visceral organs that may be normally collapsed, the saline solution will not displace blood as in the vessels but will merely open the organs and create a flow of the fluid.

The injection described above may be repeated at least once to reduce errors associated with the administration of the injection, such as, for example, where the injection does not completely displace the blood or where there is significant mixing with blood. Bifurcation(s) (with branching angle near 90 degrees) near the targeted luminal organ may potentially cause an error in the calculated $G_p$. Hence, generally the detection device should be slightly retracted or advanced and the measurement repeated. An additional application with multiple detection electrodes or a pull back or push forward during injection could accomplish the same goal. Here, an array of detection electrodes can be used to minimize or eliminate errors that would result from bifurcations or branching in the measurement or treatment site.

In an exemplary approach, error due to the eccentric position of the electrode or other imaging device can be reduced by inflation of a balloon on the device. The inflation of the balloon during measurement will place the electrodes or other imaging device in the center of the vessel away from the wall. In the case of impedance electrodes, the inflation of the balloon can be synchronized with the injection of bolus where the balloon inflation would immediately precede the bolus injection.

CSAs calculated in connection with the foregoing correspond to the area of the vessel or organ external to the device used (CSA of vessel minus CSA of the device). If the conductivity of the saline solution is determined by calibration with various tubes of known CSA, then the calibration accounts for the dimension of the device and the calculated CSA corresponds to that of the total vessel lumen as desired. In at least one embodiment, the calibration of the CSA measurement system will be performed at 37° C. by applying 100 mmHg in a solid polyphenolenoxide block with holes of known CSA ranging from 7.065 mm$^2$ (3 mm in diameter) to 1017 mm$^2$ (36 mm in diameter). If the conductivity of the solution(s) is/are obtained from a conductivity meter independent of the device, however, then the CSA of the device is generally added to the computed CSA to give the desired total CSA of the luminal organ.

The signals obtained herein are generally non-stationary, nonlinear and stochastic. To deal with non-stationary stochastic functions, one may use a number of methods, such as the Spectrogram, the Wavelet's analysis, the Wigner-Ville distribution, the Evolutionary Spectrum, Modal analysis, or preferably the intrinsic model function (IMF) method. The mean or peak-to-peak values can be systematically determined by the aforementioned signal analysis and used to compute the $G_p$ as referenced herein.

In an exemplary approach for the esophagus or the urethra, the procedures can conveniently be done by swallowing fluids of known conductances into the esophagus and infusion of fluids of known conductances into the urinary bladder followed by voiding the volume. In another approach, fluids can be swallowed or urine voided followed by measurement of the fluid conductances from samples of the fluid. The latter method can be applied to the ureter where a catheter can be advanced up into the ureter and fluids can either be injected from a proximal port on the probe (will also be applicable in the intestines) or urine production can be increased and samples taken distal in the ureter during passage of the bolus or from the urinary bladder.

In another exemplary approach, concomitant with measuring the cross-sectional area and or pressure gradient at the treatment or measurement site, a mechanical stimulus is introduced by way of inflating the balloon or by releasing a stent from the catheter, thereby facilitating flow through the stenosed part of the organ. In another approach, concomitant with measuring the cross-sectional area and or pressure gradient at the treatment site, one or more pharmaceutical substances for diagnosis or treatment of stenosis is injected into the treatment site. For example, in one approach, the injected substance can be smooth muscle agonist or antagonist. In yet another approach, concomitant with measuring the cross-sectional area and or pressure gradient at the treatment site, an inflating fluid is released into the treatment site for release of any stenosis or materials causing stenosis in the organ or treatment site.

Again, it is noted that the devices 100, systems 200, and methods 300 described herein can be applied to any body lumen or treatment site. For example, the devices 100, systems 200, and methods 300 described herein can be applied to any one of the following exemplary bodily hollow organs: the cardiovascular system including the heart, the digestive system, the respiratory system, the reproductive system, and the urogenital tract.

While various embodiments of devices and systems for obtaining parallel tissue conductance, measuring luminal cross-sectional areas, measuring fluid velocity, and/or determining plaque vulnerability using temperature and methods for using and performing the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method to obtain conductance data within a luminal organ, the method comprising the steps of:
    operating a detection device at least partially positioned within a luminal organ at a first location to obtain a first fluid temperature measurement;
    detecting a temperature change at the first location using the detection device, the temperature change indicative of an injection of a bolus of a solution having a known conductivity into the luminal organ; and
    measuring multiple output conductances using at least two impedance electrodes of the detection device prior to dilution of the bolus at the first location at least until a threshold temperature is reached.

2. The method of claim 1, further comprising the step of:
    calculating a parallel tissue conductance at the first location based in part upon the temperature change, at least one output conductance of the multiple output conductances, and the conductivity of the injected solution.

3. The method of claim 1, further comprising the steps of:
    calculating a cross-sectional area of the luminal organ at the first location based in part upon at least one output conductance of the multiple output conductances;
    selecting an appropriately-sized stent based upon the cross-sectional area; and
    implanting the stent into the luminal organ at the first location.

4. The method of claim 1, wherein the first fluid temperature measurement is a measurement of blood obtained using a thermistor of the detection device.

5. The method of claim 1, wherein the temperature change is based upon a temperature measurement at least 5° C. lower than the first fluid temperature measurement.

6. The method of claim 1, wherein the threshold temperature is within 2° C. of the first fluid temperature measurement.

7. The method of claim 1, further comprising the step of:
    obtaining a native conductance of fluid present within the luminal organ prior to injection of the bolus.

8. The method of claim 1, further comprising the step of:
    calibrating the detection device using at least one phantom immersed in a solution bath of the same solution injected into the luminal organ, wherein the solution within the solution bath is at a known temperature.

9. The method of claim 1, wherein the detection device comprises an inflatable balloon along a longitudinal axis of the detection device.

10. The method of claim 9, further comprising the step of:
    inflating the balloon to breakup materials causing a stenosis within the luminal organ.

11. The method of claim 9, wherein the detection device further comprises a stent located over the balloon, the stent capable of being distended to a desired lumen size and implanted into the luminal organ.

12. A device configured to obtain conductance data within a luminal organ, comprising:
    an elongated body having a longitudinal axis extending from a proximal end to a distal end;
    at least two electrodes located on the elongated body, the at least two electrodes configured to obtain conductance data within a luminal organ in the presence of a fluid; and
    a thermistor positioned along the longitudinal axis proximal to the at least two electrodes, the thermistor configured to obtain temperature data within the luminal organ;
    wherein the device is configured so that when a bolus of a solution having a known conductivity is injected into the luminal organ, a temperature change at a first location indicative of the bolus of the injected solution can be detected using the device prior to any dilution of the bolus at the first location, multiple output conductances in connection with the injected solution based upon the detected temperature change can be measured using the device prior to any dilution of the bolus and at least until the temperature within the luminal organ reaches a threshold temperature, and a parallel conductance at the first location based in part upon at least one output conductance of the multiple output conductances and the conductivity of the injected solution can be calculated.

13. The device of claim 12, wherein the at least two electrodes comprises at least two detection electrodes, and wherein the device further comprises at least two excitation electrodes, wherein two of the at least two detection electrodes are positioned in between two of the at least two excitation electrodes.

14. The device of claim 13, wherein at least one excitation electrode is/are in communication with a current source capable of supplying electrical current to the at least one excitation electrode.

15. The device of claim 12, configured to provide conductance data from the at least one electrode to a data acquisition and processing system capable of calculating a parallel tissue conductance and/or a cross-sectional area of the luminal organ based in part upon the conductance data and a known conductivity of a solution injected into the luminal organ.

16. The device of claim 12, wherein the elongated body is selected from the group consisting of a wire and a catheter.

17. The device of claim 12, wherein the device defines a lumen therethrough and further comprises a suction/infusion port located proximal to the at least one electrode, wherein the suction/infusion port is in communication with the lumen, thereby enabling injection of a solution into a luminal organ through the suction/infusion port.

18. The device of claim 12, wherein at least one of the at least two electrodes and the thermistor share an electrical wire connection capable of providing current to the at least one of the at least one electrodes and the thermistor.

19. A system configured to obtain conductance data within a luminal organ, comprising:
- a device, comprising:
  - an elongated body having a longitudinal axis extending from a proximal end to a distal end;
  - a detector located on the elongated body and configured to obtain conductance data within a luminal organ in the presence of a fluid; and
  - a thermistor positioned along the longitudinal axis proximal to at least one electrode of at least two electrodes of the detector, the thermistor configured to obtain temperature data within the luminal organ; and
- a data acquisition and processing system operably coupled to the device and capable of (a) receiving the temperature data from the thermistor in connection with an injection of a bolus of a solution having a known conductivity, and (b) obtaining conductance data comprising multiple conductances from the detector while receiving the temperature data.

20. The system of claim 19, wherein the elongated body is selected from the group consisting of a wire and a catheter, and wherein the data acquisition and processing system is further operable to calculate a parallel tissue conductance based in part upon at least one output conductance of the multiple conductances and the known conductivity of the solution.

* * * * *